US012599284B2

(12) United States Patent
Kamijo et al.

(10) Patent No.: US 12,599,284 B2
(45) Date of Patent: Apr. 14, 2026

(54) ENDOSCOPIC EXAMINATION SUPPORT APPARATUS, ENDOSCOPIC EXAMINATION SUPPORT METHOD, AND RECORDING MEDIUM

(71) Applicant: NEC Corporation, Tokyo (JP)

(72) Inventors: Kenichi Kamijo, Tokyo (JP); Yuji Iwadate, Tokyo (JP); Takuma Igarashi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 344 days.

(21) Appl. No.: 18/559,635

(22) PCT Filed: Jan. 11, 2023

(86) PCT No.: PCT/JP2023/000467
§ 371 (c)(1),
(2) Date: Nov. 8, 2023

(87) PCT Pub. No.: WO2024/150335
PCT Pub. Date: Jul. 18, 2024

(65) Prior Publication Data
US 2025/0095145 A1       Mar. 20, 2025

(51) Int. Cl.
*A61B 1/00*          (2006.01)
*G06T 7/00*          (2017.01)

(52) U.S. Cl.
CPC .. *A61B 1/000094* (2022.02); *A61B 1/000096* (2022.02); *G06T 7/0012* (2013.01);
(Continued)

(58) Field of Classification Search
None
See application file for complete search history.

(56) References Cited

U.S. PATENT DOCUMENTS

2020/0279373 A1*   9/2020   Hussain ................. G16H 50/70
2020/0320702 A1*  10/2020   Kamon ................. A61B 8/085
(Continued)

FOREIGN PATENT DOCUMENTS

WO       2019/138773 A1     7/2019
WO       2020/174572 A1     9/2020
(Continued)

OTHER PUBLICATIONS

Jheng, Ying-Chun, et al. "A novel machine learning-based algorithm to identify and classify lesions and anatomical landmarks in colonoscopy images." Surgical endoscopy 36.1 (2022): 640-650. (Year: 2022).*

(Continued)

*Primary Examiner* — Samah A Beg
(74) *Attorney, Agent, or Firm* — Sughrue Mion, PLLC

(57)          ABSTRACT

In the endoscopic examination support apparatus, the image acquisition means acquires an endoscopic image taken by an endoscope. The first lesion detection means detects a lesion candidate from the endoscopic image, using a machine learning model that learned a relationship between the lesion candidate and a normal state of a large intestine. The second lesion detection means detects a lesion candidate from the endoscopic image, using a machine learning model that learned a relationship between the lesion candidate and a predetermined state of the large intestine. The output means outputs at least one of a detection result of the first lesion detection means and a detection result of the second lesion detection means.

12 Claims, 21 Drawing Sheets

(52) U.S. Cl.
CPC ............... *G06T 2207/10068* (2013.01); *G06T 2207/20081* (2013.01); *G06T 2207/30028* (2013.01); *G06T 2207/30096* (2013.01)

(56) References Cited

U.S. PATENT DOCUMENTS

| | | | |
|---|---|---|---|
| 2020/0337537 A1 | 10/2020 | Hirasawa et al. | |
| 2021/0012495 A1* | 1/2021 | Kamon | G16H 50/20 |
| 2021/0385367 A1* | 12/2021 | Yabe | G16H 40/67 |
| 2023/0100147 A1* | 3/2023 | Kubota | G06V 10/764 |
| | | | 382/128 |
| 2023/0141302 A1* | 5/2023 | Demura | A61B 1/045 |
| 2023/0245311 A1 | 8/2023 | Takahashi | |
| 2023/0281968 A1* | 9/2023 | Kobayashi | G06V 10/774 |
| | | | 382/128 |

FOREIGN PATENT DOCUMENTS

| | | |
|---|---|---|
| WO | 2020/254845 A1 | 12/2020 |
| WO | 2022/014235 A1 | 1/2022 |
| WO | 2022/025151 A1 | 2/2022 |
| WO | 2022/029824 A1 | 2/2022 |
| WO | 2023/276158 A1 | 1/2023 |

OTHER PUBLICATIONS

Ding, Zhen, et al. "Gastroenterologist-level identification of small-bowel diseases and normal variants by capsule endoscopy using a deep-learning model." Gastroenterology 157.4 (2019): 1044-1054. (Year: 2019).*

International Search Report for PCT Application No. PCT/JP2023/000467, mailed on Mar. 7, 2023.

US Office Action for U.S. Appl. No. 18/531,859, mailed on Dec. 23, 2025.

Owais, Muhammad, et al. "Automated diagnosis of various gastro-intestinal lesions using a deep learning-based classification and retrieval framework with a large endoscopic database: model development and validation." Journal of medical Internet research 22.11 (2020): e18563. (Year: 2020).

\* cited by examiner

100 : ENDOSCOPIC EXAMINATION SYSTEM

Figure 12:
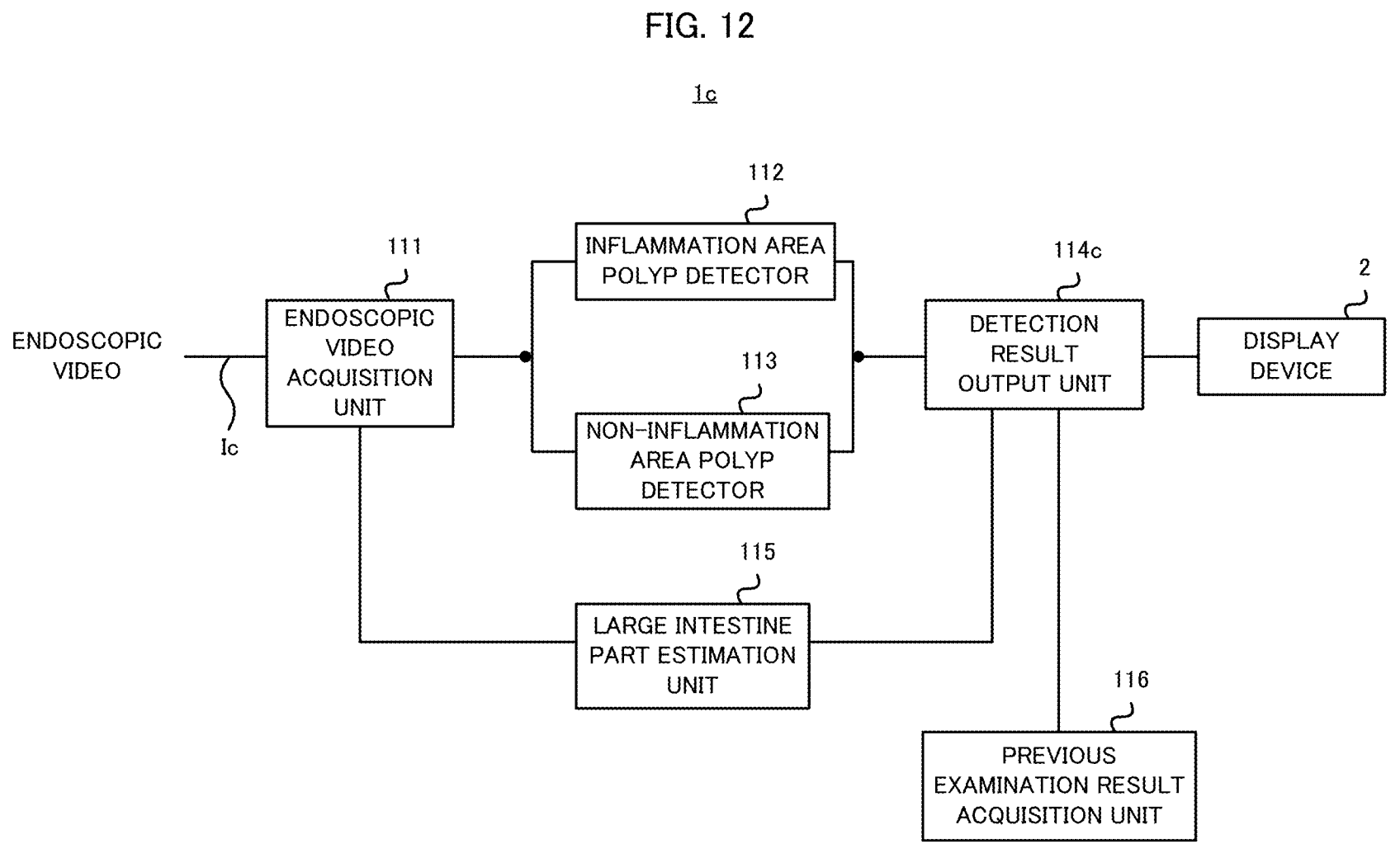

ENDOSCOPIC VIDEO

1c

111 ENDOSCOPIC VIDEO ACQUISITION UNIT

112 INFLAMMATION AREA POLYP DETECTOR

113 NON-INFLAMMATION AREA POLYP DETECTOR

114c DETECTION RESULT OUTPUT UNIT

115 LARGE INTESTINE PART ESTIMATION UNIT

116 PREVIOUS EXAMINATION RESULT ACQUISITION UNIT

2 DISPLAY DEVICE

Figure 14:
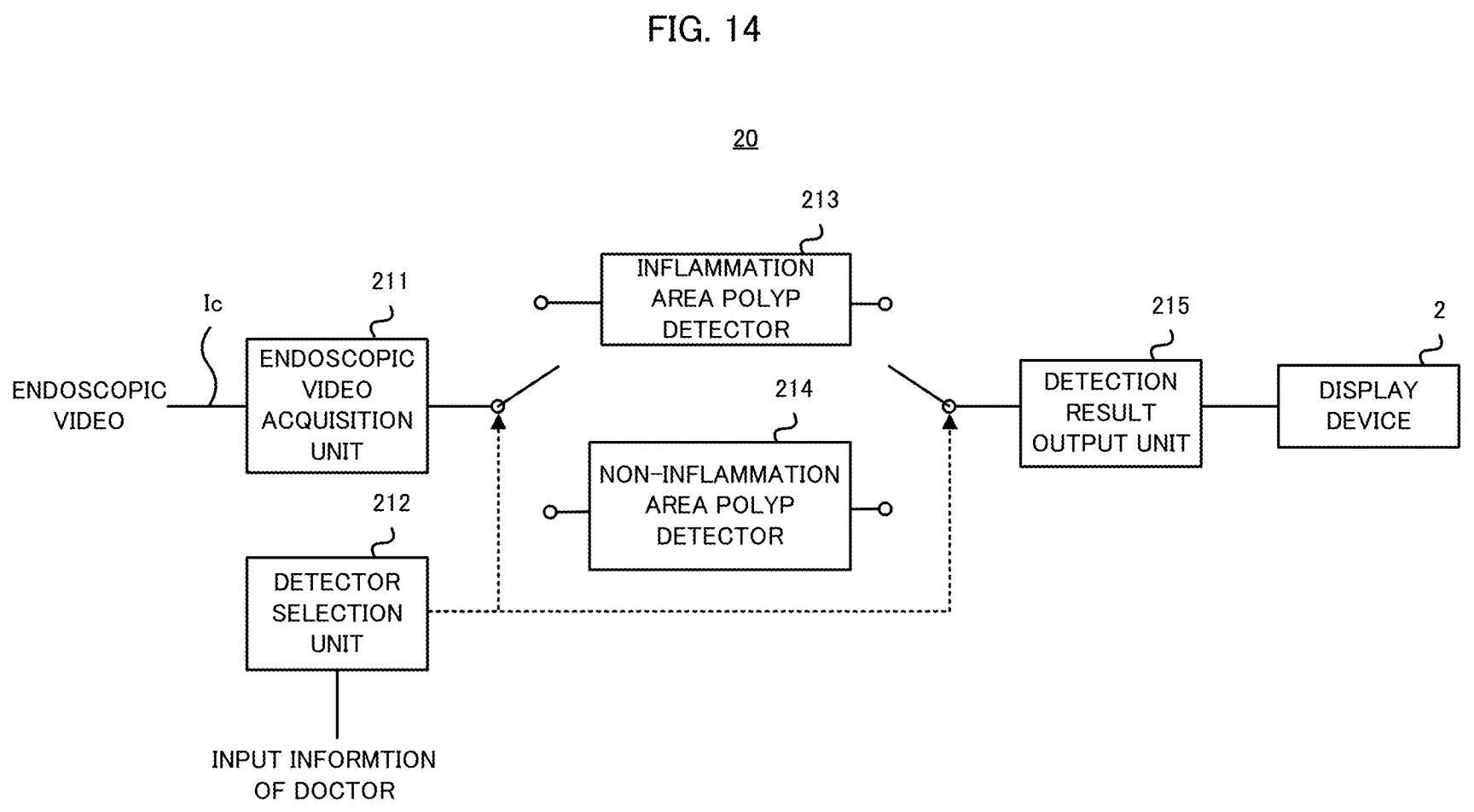

ENDOSCOPIC VIDEO

Ic

211 ENDOSCOPIC VIDEO ACQUISITION UNIT

212 DETECTOR SELECTION UNIT

INPUT INFORMTION OF DOCTOR

213 INFLAMMATION AREA POLYP DETECTOR

214 NON-INFLAMMATION AREA POLYP DETECTOR

215 DETECTION RESULT OUTPUT UNIT

2 DISPLAY DEVICE

Figure 16:
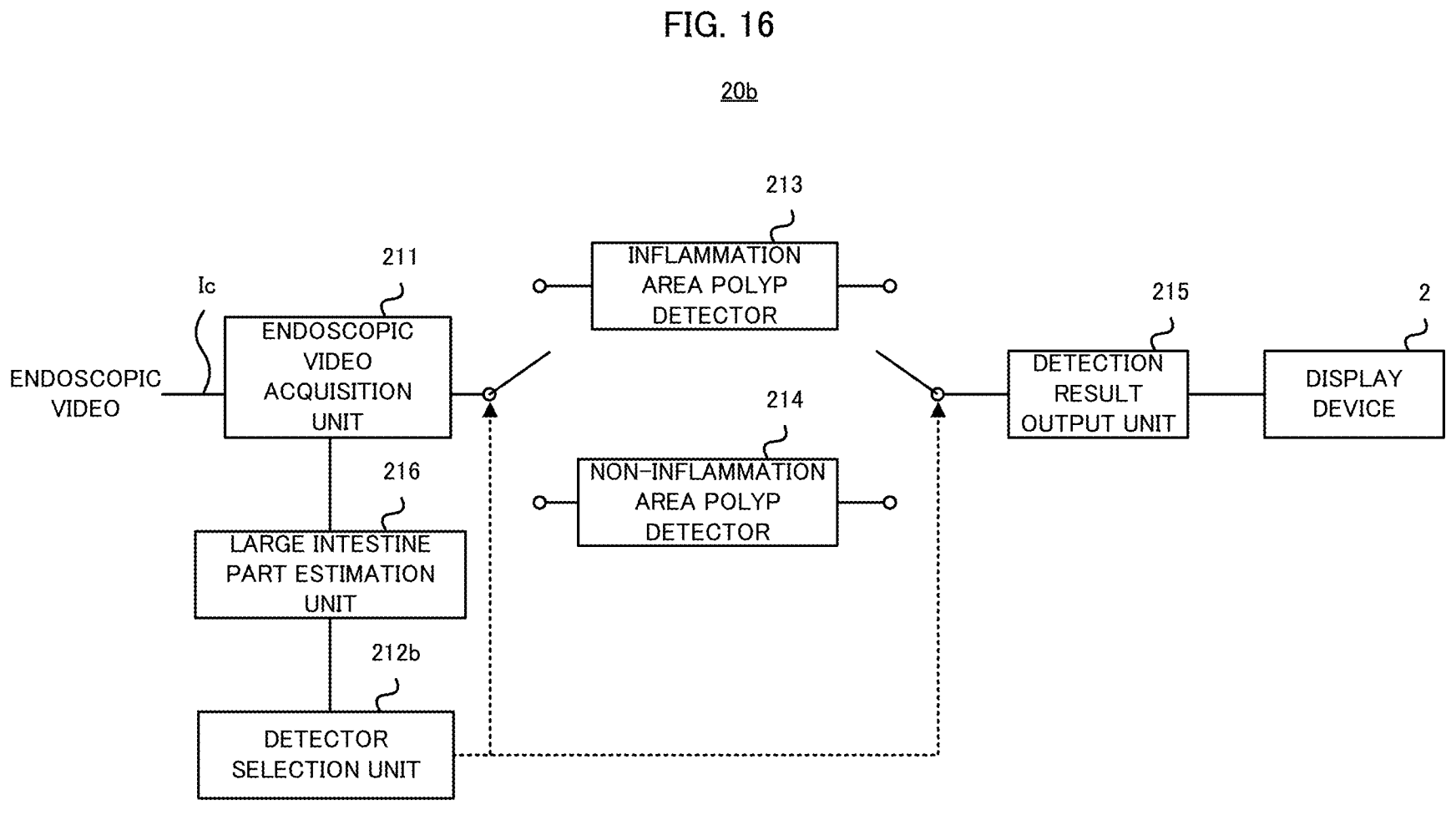

ENDOSCOPIC VIDEO

Ic

211 — ENDOSCOPIC VIDEO ACQUISITION UNIT

216 — LARGE INTESTINE PART ESTIMATION UNIT

212b — DETECTOR SELECTION UNIT

213 — INFLAMMATION AREA POLYP DETECTOR

214 — NON-INFLAMMATION AREA POLYP DETECTOR

215 — DETECTION RESULT OUTPUT UNIT

2 — DISPLAY DEVICE

FIG. 19

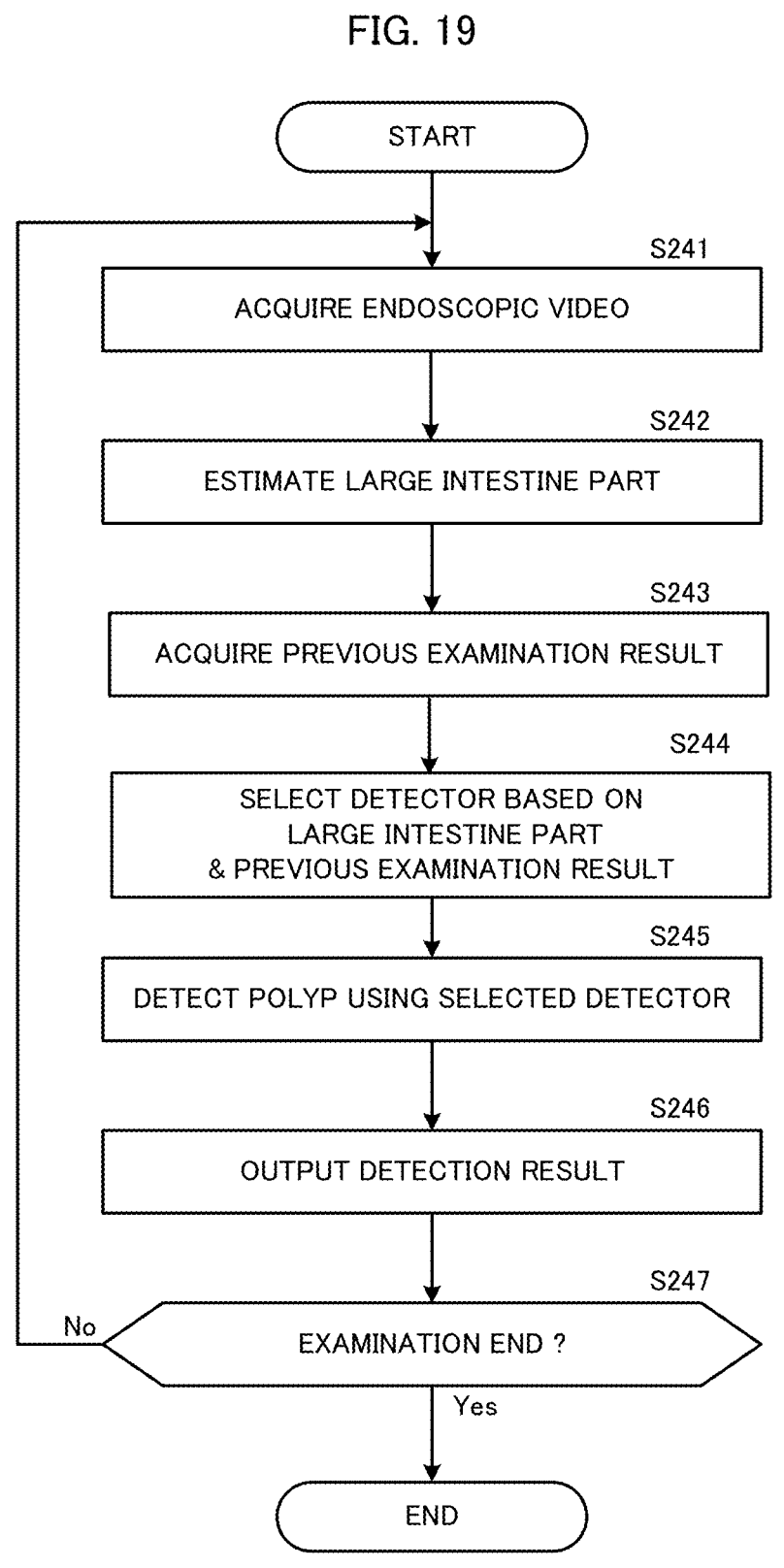

```
          ┌──────────────┐
          │    START     │
          └──────┬───────┘
                 │
   ┌─────────────┤
   │             ▼                              S241
   │   ┌─────────────────────────────────────┐
   │   │   ACQUIRE ENDOSCOPIC VIDEO           │
   │   └─────────────────┬───────────────────┘
   │                     ▼                      S242
   │   ┌─────────────────────────────────────┐
   │   │   ESTIMATE LARGE INTESTINE PART      │
   │   └─────────────────┬───────────────────┘
   │                     ▼                      S243
   │   ┌─────────────────────────────────────┐
   │   │ ACQUIRE PREVIOUS EXAMINATION RESULT  │
   │   └─────────────────┬───────────────────┘
   │                     ▼                      S244
   │   ┌─────────────────────────────────────┐
   │   │      SELECT DETECTOR BASED ON        │
   │   │       LARGE INTESTINE PART           │
   │   │   & PREVIOUS EXAMINATION RESULT      │
   │   └─────────────────┬───────────────────┘
   │                     ▼                      S245
   │   ┌─────────────────────────────────────┐
   │   │ DETECT POLYP USING SELECTED DETECTOR │
   │   └─────────────────┬───────────────────┘
   │                     ▼                      S246
   │   ┌─────────────────────────────────────┐
   │   │      OUTPUT DETECTION RESULT         │
   │   └─────────────────┬───────────────────┘
   │                     ▼                      S247
   │   No  ╱───────────────────────────────╲
   └──────<       EXAMINATION END ?          >
          ╲───────────────────────────────╱
                         │ Yes
                         ▼
          ┌──────────────┐
          │     END      │
          └──────────────┘
```

FIG. 21

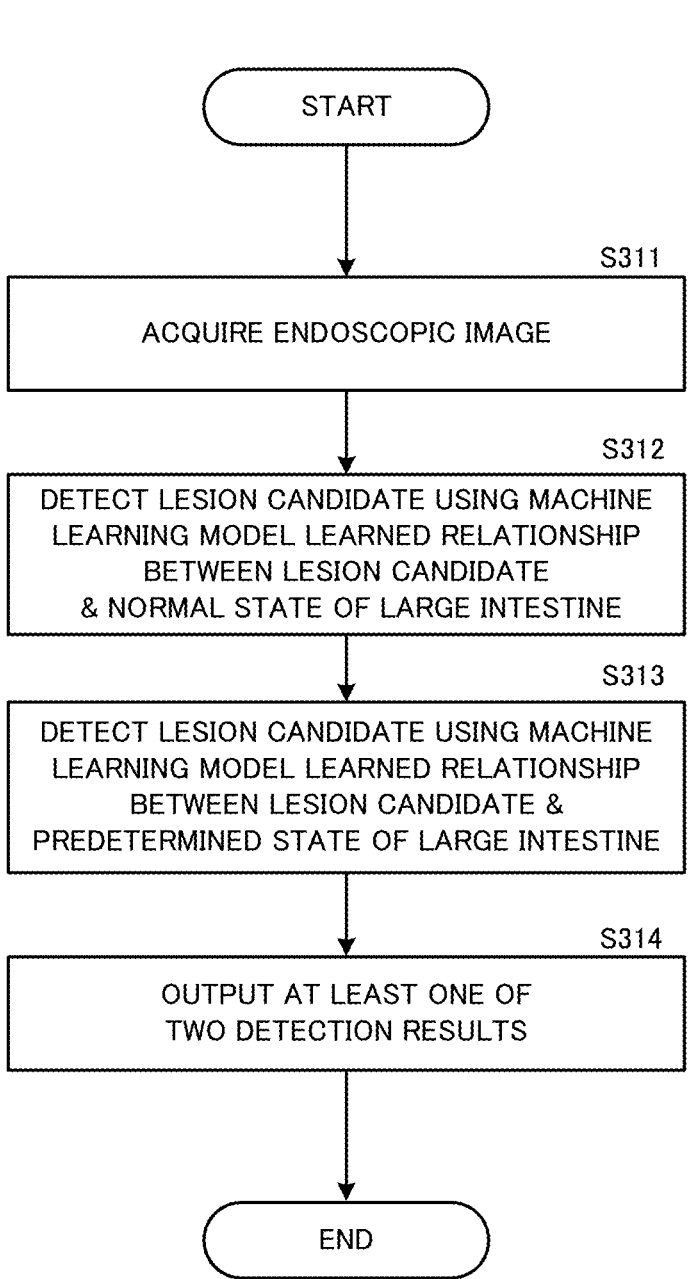

START

S311

ACQUIRE ENDOSCOPIC IMAGE

S312

DETECT LESION CANDIDATE USING MACHINE
LEARNING MODEL LEARNED RELATIONSHIP
BETWEEN LESION CANDIDATE
& NORMAL STATE OF LARGE INTESTINE

S313

DETECT LESION CANDIDATE USING MACHINE
LEARNING MODEL LEARNED RELATIONSHIP
BETWEEN LESION CANDIDATE &
PREDETERMINED STATE OF LARGE INTESTINE

S314

OUTPUT AT LEAST ONE OF
TWO DETECTION RESULTS

END

ENDOSCOPIC EXAMINATION SUPPORT APPARATUS, ENDOSCOPIC EXAMINATION SUPPORT METHOD, AND RECORDING MEDIUM

This application is a National Stage Entry of PCT/JP2023/000467 filed on Jan. 11, 2023, the contents of all of which are incorporated herein by reference, in their entirety.

TECHNICAL FIELD

The present disclosure relates to support for endoscopic examination.

BACKGROUND ART

Popularization of AI (Artificial Intelligence) for detecting lesions from images and moving images taken in the endoscopic examination is advancing. However, detecting lesions with high accuracy is difficult depending on the condition of the patient's large intestine, for example, when there is inflammation in the large intestine. Patent Document 1 proposes an endoscopic examination support system that allows a user to select a discriminator in his or her own preference from a plurality of discriminators.

PRECEDING TECHNICAL REFERENCES

Patent Document

Patent Document 1: International Publication WO2022-029824

SUMMARY

Problem to be Solved

However, even by Patent Document 1, it is not always possible to appropriately detect lesions depending on the state of the large intestine.

It is an object of the present disclosure to provide an endoscopic examination support apparatus capable of detecting lesions in consideration of the condition of the large intestine.

Means for Solving the Problem

According to an example aspect of the present invention, there is provided an endoscopic examination support apparatus comprising:

an image acquisition means configured to acquire an endoscopic image taken by an endoscope;

a first lesion detection means configured to detect a lesion candidate from the endoscopic image, using a machine learning model that learned a relationship between the lesion candidate and a normal state of a large intestine;

a second lesion detection means configured to detect a lesion candidate from the endoscopic image, using a machine learning model that learned a relationship between the lesion candidate and a predetermined state of the large intestine; and an output means configured to output at least one of a detection result of the first lesion detection means and a detection result of the second lesion detection means.

According to another example aspect of the present invention, there is provided an endoscopic examination support method comprising:

acquiring an endoscopic image taken by an endoscope;

detecting a lesion candidate from the endoscopic image, using a machine learning model that learned a relationship between the lesion candidate and a normal state of a large intestine;

detecting a lesion candidate from the endoscopic image, using a machine learning model that learned a relationship between the lesion candidate and a predetermined state of the large intestine; and outputting at least one of two detection results of the lesion candidate.

According to still another example aspect of the present invention, there is provided a recording medium storing a program, the program causing a computer to perform processing of:

acquiring an endoscopic image taken by an endoscope;

detecting a lesion candidate from the endoscopic image, using a machine learning model that learned a relationship between the lesion candidate and a normal state of a large intestine;

detecting a lesion candidate from the endoscopic image, using a machine learning model that learned a relationship between the lesion candidate and a predetermined state of the large intestine; and outputting at least one of two detection results of the lesion candidate.

Effect

According to the present disclosure, it is possible to detect lesions in consideration of the state of the large intestine.

BRIEF DESCRIPTION OF THE DRAWINGS

FIG. 2 is a block diagram showing a hardware configuration of an endoscopic examination support apparatus.

FIG. 12 is a block diagram showing a functional configuration of an endoscopic examination support apparatus according to a fourth example of the first example embodiment.

FIG. 14 is a block diagram showing a functional configuration of an endoscopic examination support apparatus according to a first example of a second example embodiment.

FIG. 16 is a block diagram showing a functional configuration of an endoscopic examination support apparatus according to a second example of the second example embodiment.

FIG. 19 is a flowchart of image display processing by the endoscopic examination support apparatus according to the third example of the second example embodiment.

FIG. 21 is a flowchart of processing by the endoscopic examination support apparatus according to the third example embodiment.

EXAMPLE EMBODIMENTS

Preferred example embodiments of the present disclosure will be described with reference to the accompanying drawings.

First Example Embodiment

First Example (System Configuration)

Figure 1:
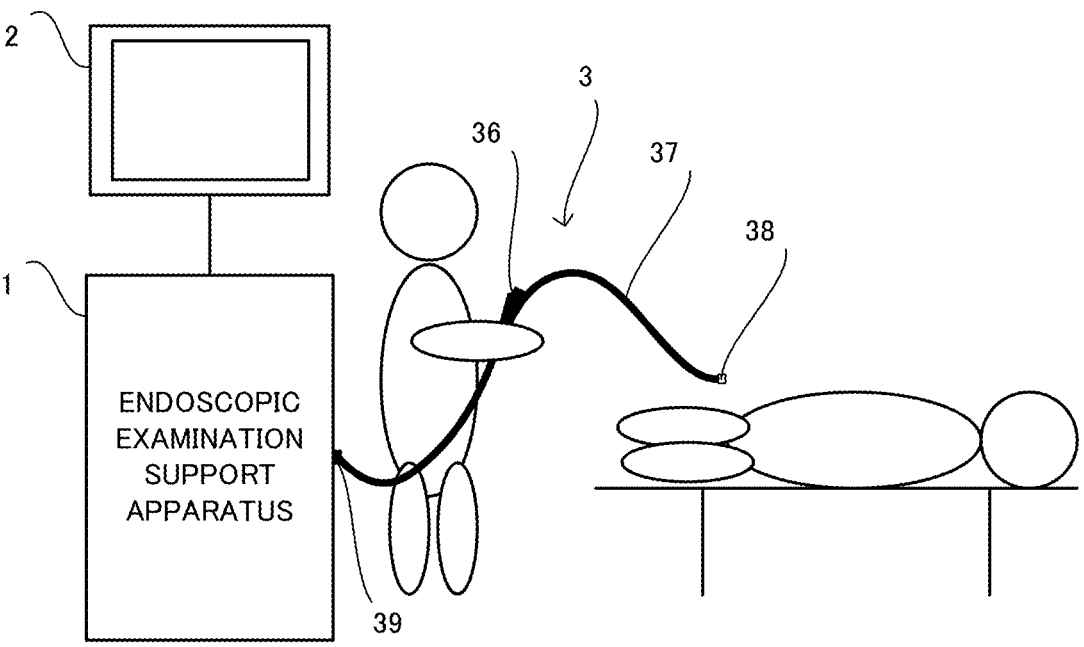
FIG. 1 is a block diagram showing a schematic configuration of an endoscopic examination system.

FIG. 1 shows a schematic configuration of an endoscopic examination system 100. The endoscopic examination system 100 detects lesions at the time of examination (including treatment) using an endoscope and displays a result. In particular, the endoscopic examination system 100 of the present example embodiment is characterized in that it is provided with different lesion detectors and it is possible to switch and display the detection result of the lesion detector depending on the state of the large intestine. Thus, it becomes possible to detect lesion candidates with high accuracy.

In the present example embodiment, the state of the large intestine refers to a state in which inflammation occurs in the large intestine and a state in which inflammation does not occur in the large intestine (non-inflammation). The endoscopic examination system 100 includes a lesion detector for inflammation areas and a lesion detector for non-inflammation areas, as the different lesion detectors.

As shown in FIG. 1, the endoscopic examination system 100 mainly includes an endoscopic examination support apparatus 1, a display device 2, and an endoscope 3 connected to the endoscopic examination support apparatus 1.

The endoscopic examination support apparatus 1 acquires a video (i.e., a moving image; hereinafter also referred to as an "endoscopic video Ic") captured by the endoscope 3 during the endoscopic examination from the endoscope 3 and displays display data for confirmation by an examiner (doctor) of the endoscopic examination on the display device 2. Specifically, the endoscopic examination support apparatus 1 acquires a video of an inside of an organ captured by the endoscope 3 as an endoscopic video Ic during the endoscopic examination. In addition, the doctor operates the endoscope 3 to input the photographing instruction of the position of a lesion, when the lesion is found during the endoscopic examination. The endoscopic examination support apparatus 1 generates a lesion image showing the position of the lesion based on the photographing instruction by the doctor. Specifically, the endoscopic examination support apparatus 1 generates a lesion image which is a still image, based on the photographing instruction of the doctor, from the endoscopic video Ic which is a moving image.

The display device 2 is a display to perform predetermined display on the basis of a display signal supplied from the endoscopic examination support apparatus 1.

The endoscope 3 mainly includes an operation unit 36 used by a doctor to input instructions such as air supply, water supply, angle adjustment, and a photographing instruction, a shaft 37 having flexibility and inserted into an organ of a subject to be examined, a tip portion 38 with an imaging unit such as an ultra-compact imaging element, and a connection unit 39 for connection with the endoscopic examination support apparatus 1.

While the following explanation is mainly directed to the processing in an endoscopic examination of a large intestine, the examination target may be a gastrointestinal tract (digestive organs) such as the stomach, esophagus, small intestine, and duodenum, as well as the large intestine.

[Hardware Configuration]

Figure 2:
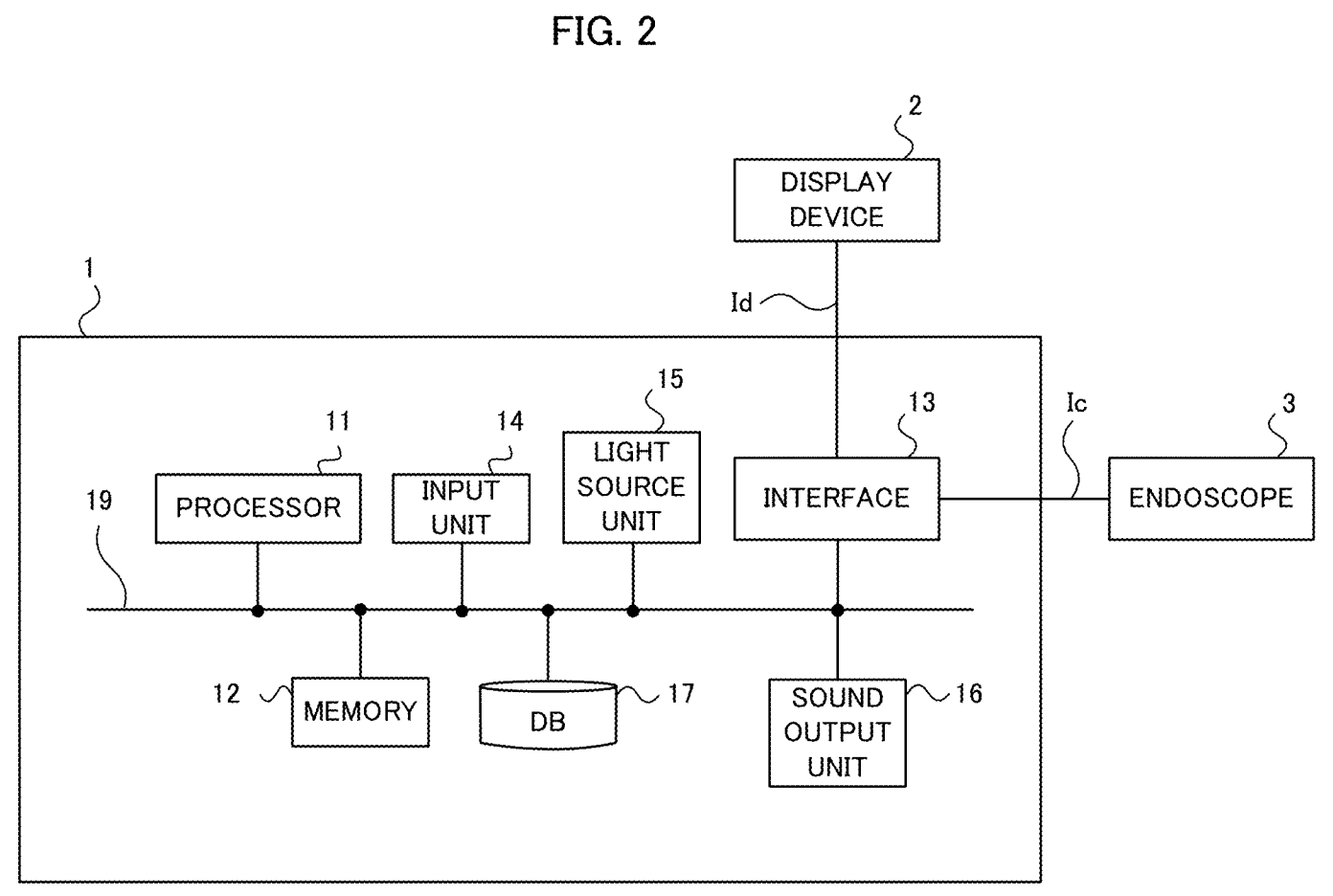

FIG. 2 shows a hardware configuration of the endoscopic examination support apparatus 1. The endoscopic examination support apparatus 1 mainly includes a processor 11, a memory 12, an interface 13, an input unit 14, a light source unit 15, a sound output unit 16, and a data base (hereinafter referred to as "DB") 17. Each of these elements is connected via a data bus 19.

The processor 11 executes a predetermined processing by executing a program stored in the memory 12. The processor 11 is a processor such as a CPU (Central Processing Unit), a GPU (Graphics Processing Unit), and a TPU (Tensor Processing Unit). The processor 11 may be configured by a plurality of processors. The processor 11 is an example of a computer.

The memory 12 is configured by various volatile memories used as a working memory and non-volatile memories for storing information needed for processing by the endoscopic examination support apparatus 1, such as a RAM (Random Access Memory) and a ROM (Read Only Memory). Incidentally, the memory 12 may include an external storage device such as a hard disk connected to or incorporated in the endoscopic examination support apparatus 1, and may include a storage medium such as a removable flash memory or a disk medium. The memory 12 stores a program for the endoscopic examination support apparatus 1 to execute each process in the present example embodiment.

Also, the memory 12 temporarily stores a series of endoscopic videos Ic captured by the endoscope 3 during the endoscopic examination, based on the control of the processor 11. Also, the memory 12 temporarily stores the lesion images captured based on the photographing instruction of the doctor during the endoscopic examination. These images are stored in the memory 12 in association with information such as an identification information of a subject (e.g., a patient ID) and a time stamp.

The interface 13 performs an interface operation between the endoscopic examination support apparatus 1 and the external devices. For example, the interface 13 supplies the display data Id generated by the processor 11 to the display device 2. Also, the interface 13 supplies the illumination light generated by the light source unit 15 to the endoscope 3. Also, the interface 13 supplies an electrical signal indicating the endoscopic video Ic supplied from the endoscope 3 to the processor 11. The interface 13 may be a communication interface such as a network adapter for wired or wireless communication with an external device, or may be a hardware interface compliant with a USB (Universal Serial Bus), SATA (Serial Advanced Technology Attachment), etc.

The input unit 14 generates an input signal based on the operation of the doctor. The input unit 14 is, for example, a button, a touch panel, a remote controller, a voice input device, or the like. The light source unit 15 generates light to be delivered to the tip portion 38 of the endoscope 3. The light source unit 15 may also incorporate a pump or the like for delivering water or air to be supplied to the endoscope 3. The sound output unit 16 outputs the sound based on the control of the processor 11.

The DB 17 stores the endoscopic images and the lesion information acquired by the previous endoscopic examination of the subject. The lesion information includes lesion images and information associated with the lesion (hereinafter referred to as "associated information"). The DB 17 may include an external storage device such as a hard disk connected to or incorporated in the endoscopic examination support apparatus 1, and may include a storage medium such as a removable flash memory. Instead of providing the DB 17 in the endoscopic examination system 100, the DB 17 may be provided in an external server or the like to acquire relevant information from the server through communication.

(Functional Configuration)

Figure 3:
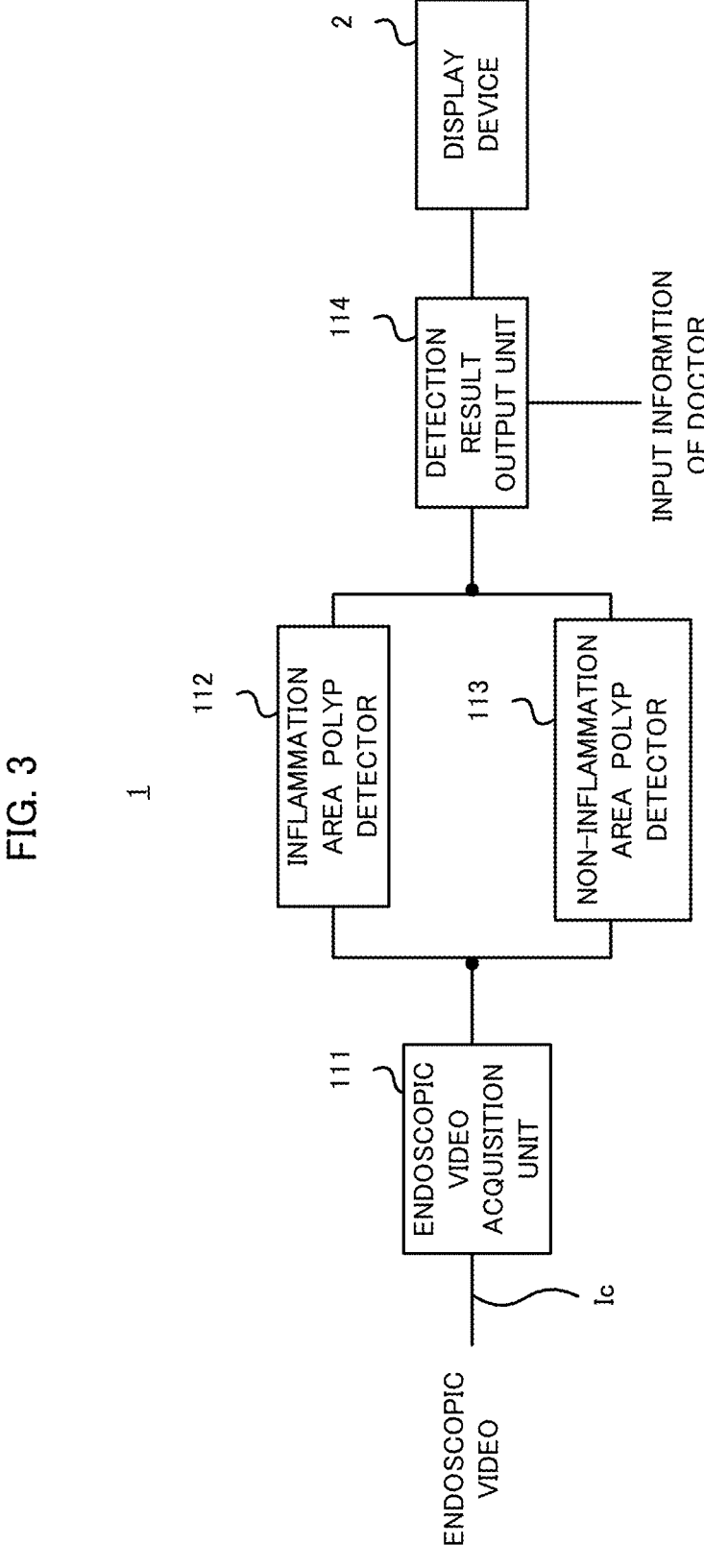
FIG. 3 is a block diagram showing a functional configuration of an endoscopic examination support apparatus according to a first example of a first example embodiment.

FIG. 3 is a block diagram illustrating a functional configuration of the endoscope examination support apparatus 1 according to a first example. The endoscopic examination support apparatus 1 functionally includes, in addition to the display device 2 described above, an endoscopic video acquisition unit 111, an inflammation area polyp detector 112, a non-inflammation area polyp detector 113, and a detection result output unit 114.

To the endoscopic examination support apparatus 1, the endoscopic video Ic is inputted from the endoscope 3. The endoscopic video Ic is inputted to the endoscopic video acquisition unit 111. The endoscopic video acquisition unit 111 outputs the inputted endoscopic video Ic to the inflammation area polyp detector 112 and the non-inflammation area polyp detector 113.

The inflammation area polyp detector 112 acquires the endoscopic video Ic from the endoscopic video acquisition unit 111. Then, the inflammation area polyp detector 112 detects a lesion candidate (hereinafter, also referred to as a "polyp") from the endoscopic video Ic by using an image recognition model prepared in advance. This image recognition model is a model learned in advance so as to estimate a polyp existing in the inflammation area, and is hereinafter referred to as "an inflammation area polyp detection model".

When the inflammation area polyp detector 112 detects a polyp, it calculates a confidence score of the polyp. The confidence score is a score indicating a likelihood of a polyp. The confidence score is, for example, a value larger than or equal to 0 and smaller than or equal to 1. The closer the confidence score is to 1, the higher the likelihood of a polyp is. In addition, when the inflammation area polyp detector 112 detects a polyp, it generates figure information including the polyp position and the polyp shape. Then, the inflammation area polyp detector 112 outputs the confidence score and the figure information to the detection result output unit 114 as the detection result (hereinafter, referred to as "inflammation area polyp detection result").

The non-inflammation area polyp detector 113 acquires the endoscopic video Ic from the endoscopic video acquisition unit 111. Then, the non-inflammation area polyp detector 113 detects a polyp from the endoscopic video Ic using an image recognition model prepared in advance. This image recognition model is a model learned in advance so as to estimate a polyp existing in a non-inflammation area, and is hereinafter referred to as a "non-inflammation area polyp detection model".

When the non-inflammation area polyp detector 113 detects a polyp, it calculates the confidence score of the polyp. In addition, when the non-inflammation area polyp detector 113 detects a polyp, it generates figure information including the polyp position and the polyp shape. Then, the non-inflammation area polyp detector 113 outputs the confidence score and the figure information to the detection result output unit 114 as the detection result (hereinafter, referred to as "non-inflammation area polyp detection result").

The detection result output unit 114 acquires the inflammation area polyp detection result from the inflammation area polyp detector 112 and acquires the non-inflammation area polyp detection result from the non-inflammation area polyp detector 113. Also, the detection result output unit 114 acquires input information of the doctor.

Here, the input information of the doctor includes instruction information for instructing switching of the display content. Specifically, the doctor operates the touch panel of the endoscopic examination support apparatus 1 and/or the operation unit 36 of the endoscope 3 to input the instruction information to display the inflammation area polyp detection result or the non-inflammation area polyp detection result. Incidentally, the input of the instruction information by the doctor is performed at any timing during the endoscopic examination.

Figure 4A:
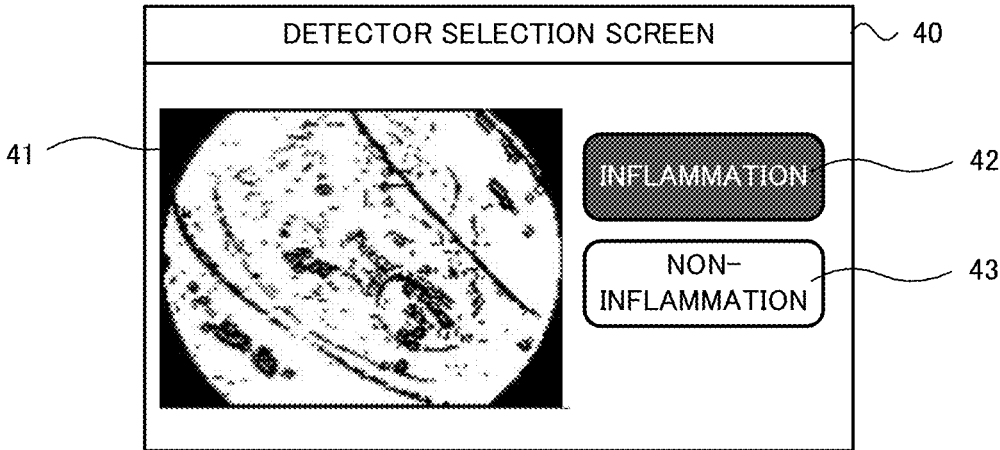
FIGS. 4A to 4C show an example of an input of instruction information by a doctor.
Figure 4B:
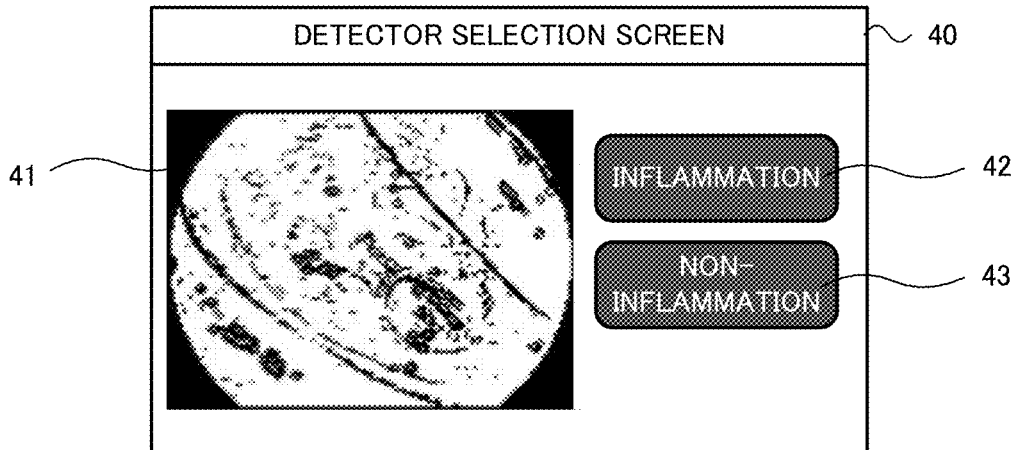
Figure 4C:
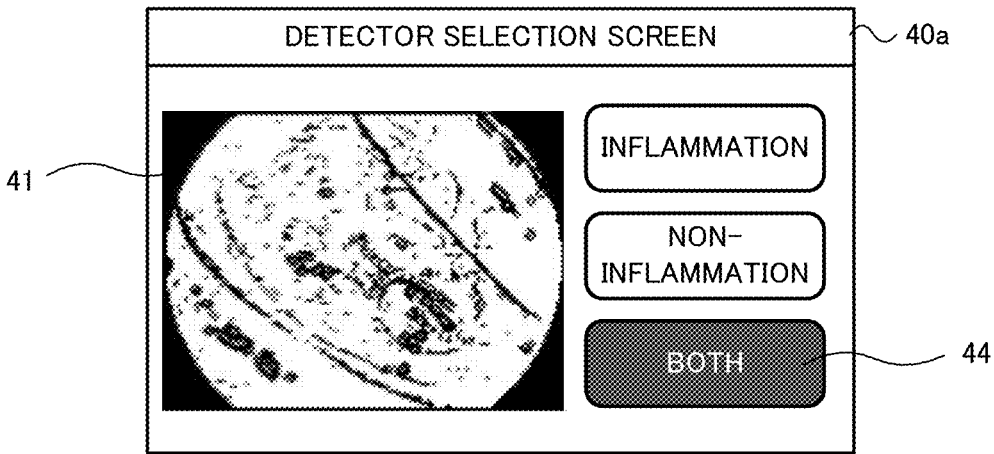

FIGS. 4A to 4C shows an example of input of the instruction information by a doctor. In FIG. 4A, a detector selection screen 40 is displayed on the touch panel of the endoscopic examination support apparatus 1. The detector selection screen 40 includes an endoscopic video 41, an inflammation button 42, and a non-inflammation button 43. The endoscopic video 41 is the endoscopic video Ic obtained during the endoscopic examination. The inflammation button 42 is an instruction input button for displaying the inflammation area polyp detection result. The non-inflammation button 43 is an instruction input button for displaying the non-inflammation area polyp detection result. In FIG. 4A, the inflammation button 42 is colored, indicating that the inflammation button 42 is being selected by the doctor.

In FIG. 4B, the inflammation button 42 and the non-inflammation button 43 are colored, indicating that both buttons are being selected by the doctor. By the input as shown in FIG. 4B, the doctor can display both the inflammation area polyp detection result and the non-inflammation area polyp detection result (hereinafter, referred to as "both polyp detection results"). The detector selection screen 40 may include an instruction input button for displaying both polyp detection results. For example, in FIG. 4C, the detector selection screen 40*a* includes the both button 44. By selecting the both button 44, the doctor can display the both polyp detection results at the same time.

Returning to FIG. 3, the detection result output unit 114 selects at least one of the inflammation area polyp detection result and the non-inflammation area polyp detection result based on the input information of the doctor. Then, the detection result output unit 114 generates display data using the selected polyp detection result and outputs the generated display data to the display device 2.

In the above-described configuration, the endoscopic video acquisition unit 111 is an example of an image acquisition means, the inflammation area polyp detector 112 is an example of a second lesion detection means, the non-inflammation area polyp detector 113 is an example of a first lesion detection means, and the detection result output unit 114 is an example of an output means.

Display Example

Figure 5A:
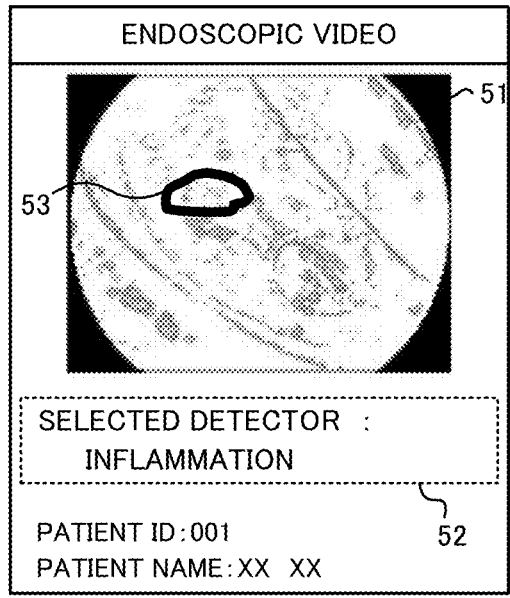
FIGS. 5A to 5D show a display example by a display device.

Next, a display example by the display device 2 will be described. FIG. 5 is an example of a display by the display device 2. FIG. 5A shows a display example of the inflammation area polyp detection result. In FIG. 5A, an endoscopic video 51, a currently-selected detector 52, and an inflammation polyp area 53 are displayed on the display device 2. The endoscopic video 51 is the endoscopic video Ic obtained during the endoscopic examination. The selected detector 52 indicates the polyp detector being selected. For example, if the doctor instructs to display the inflammation area polyp detection result, "INFLAMMATION" is displayed on the currently-selected detector 52. On the other hand, if the doctor instructs to display the non-inflammation area polyp detection result, "NON-INFLAMMATION" is displayed on the currently-selected detector 52. In FIG. 5A, "INFLAMMATION" is displayed on the currently-selected detector 52, and the inflammation polyp area 53 is superimposed and displayed on the endoscopic video 51. The inflammation polyp area 53 is a polyp area generated based on the inflammation area polyp detection result.

Figure 5B:
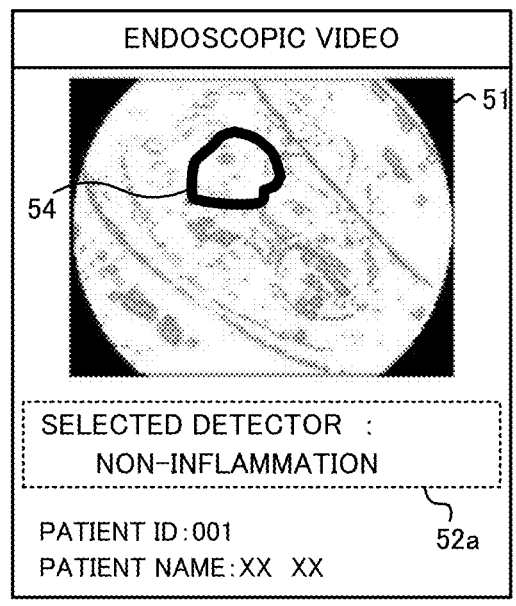

FIG. 5B shows a display example of the non-inflammation area polyp detection result. In FIG. 5B, "NON-INFLAMMATION" is displayed on the currently-selected detector 52*a*, and the non-inflammation polyp area 54 is superimposed and displayed on the endoscopic video 51. The non-inflammation polyp area 54 is a polyp area generated based on the non-inflammation area polyp detection result.

Figure 5C:
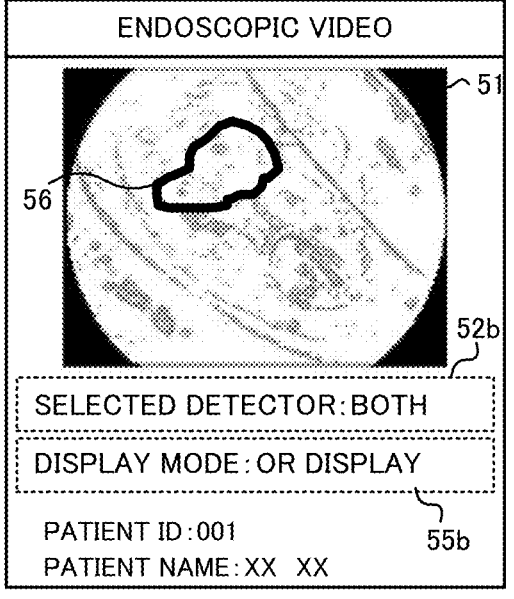
Figure 5D:
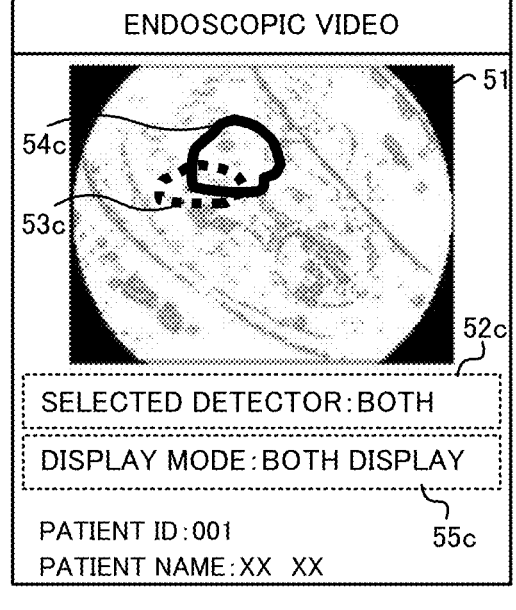

FIGS. 5C and 5D show a display example of the both polyp detection results. In FIGS. 5C and 5D, "BOTH" are displayed on the currently-selected detectors 52*b* and 52*c*. "BOTH" indicates that the doctor instructed to display the both polyp detection results. Further, in FIGS. 5C and 5D, the display mode 55*b* and the display mode 55*c* are displayed on the display device 2. The display mode 55*b* and the display mode 55*c* indicate the display mode of the polyp area. The display mode of the polyp area can be determined in advance by the doctor.

For example, in FIG. 5C, the "OR DISPLAY" mode is selected as the display mode. The "OR DISPLAY" mode is a mode in which a result of adding the inflammation polyp area and the non-inflammation polyp area is displayed. In FIG. 5C, the polyp area 56 is superimposed on the endoscopic video 51 as a result of the addition of the inflammation polyp area and the non-inflammation polyp area.

Further, in FIG. 5D, the "BOTH DISPLAY" mode is selected as the display mode. The "BOTH DISPLAY" mode is a mode in which the inflammation polyp area and the non-inflammation polyp area are displayed in different manners. In FIG. 5D, the inflammation polyp area 53*c* is superimposed on the endoscopic video 51 by a broken line, and the non-inflammation polyp area 54*c* is superimposed on the endoscopic video 51 by a solid line. Other than the above, only the overlapping portion of the inflammation polyp area and the non-inflammation polyp area may be superimposed on the endoscopic video 51. Also, both polyp detection results may be integrated using NMS (Non-Maximum Suppression) or WBF (Weighted Box Fusion) to be superimposed on the endoscopic video 51 as the polyp area.

(Image Display Processing)

Figure 6:
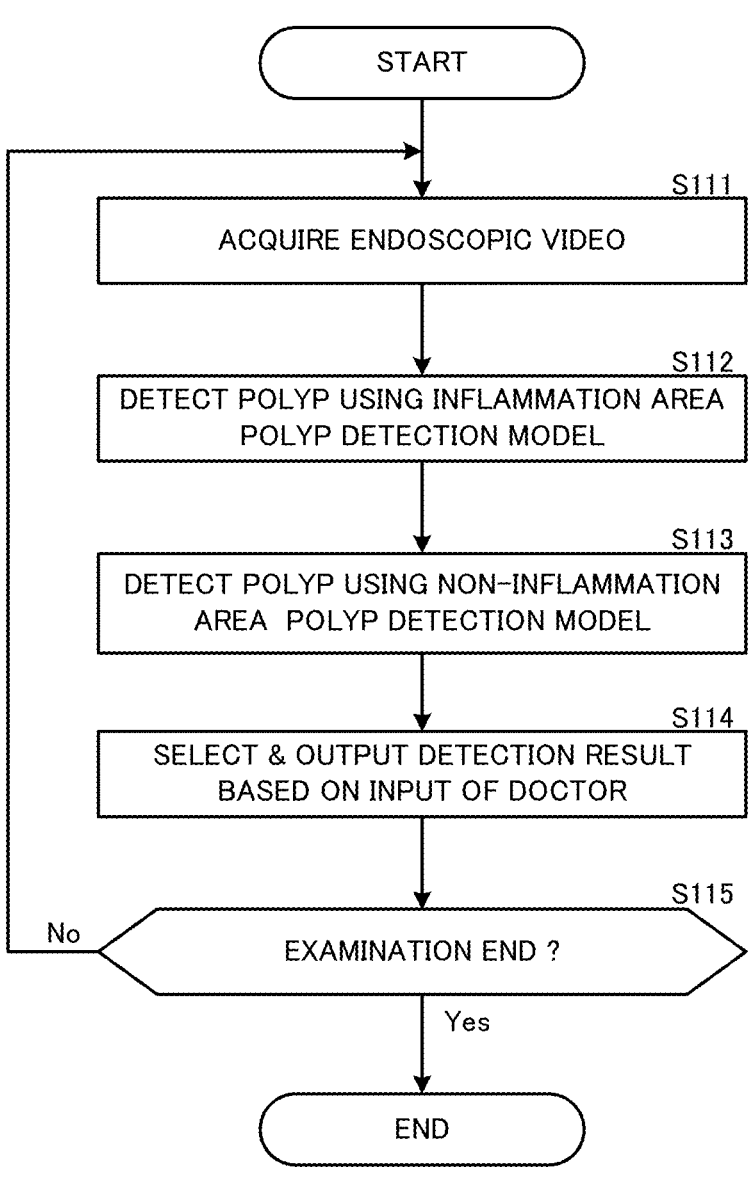
FIG. 6 is a flowchart of image display processing by the endoscopic examination support apparatus according to the first example of the first example embodiment.

Next, image display processing for performing the above-described display will be described. FIG. 6 is a flowchart of image display processing by the endoscopic examination support apparatus 1. This processing is realized by the processor 11 shown in FIG. 2, which executes a pre-prepared program and operates as each element shown in FIG. 3.

First, the endoscopic video Ic is inputted from the endoscope 3 to the endoscopic examination support apparatus 1. The endoscopic video acquisition unit 111 acquires the endoscopic video Ic and outputs it to the inflammation area polyp detector 112 and the non-inflammation area polyp detector 113 (step S111).

Next, the inflammation area polyp detector 112 detects the polyp from the endoscopic video Ic using the inflammation area polyp detection model. The inflammation area polyp detector 112 outputs the inflammation area polyp detection result to the detection result output unit 114 (step S112).

Next, the non-inflammation area polyp detector 113 detects the polyp from the endoscopic video Ic using the non-inflammation area polyp detection model. The non-inflammation area polyp detector 113 outputs the non-inflammation area polyp detection result to the detection result output unit 114 (step S113).

Next, the detection result output unit 114 acquires input information of the doctor. The input information of the doctor includes instruction information of switching of the display content. The detection result output unit 114 selects at least one of the inflammation area polyp detection result and the non-inflammation area polyp detection result based on the input information of the doctor. Then, the detection result output unit 114 generates display data by using the selected polyp detection result, and outputs the display data to the display device 2 (step S114).

Next, the endoscopic examination support apparatus 1 determines whether or not the examination is completed. For example, the endoscopic examination support apparatus 1 determines that the examination is completed when the doctor performs an operation of ending the examination on the endoscopic examination support apparatus 1 or the endoscope 3. Further, the endoscopic examination support apparatus may automatically determine that the examination is completed when it is determined that the captured image becomes an image outside the organ by the image analysis of the captured image by the endoscope 3. If it is determined that the examination not is completed (step S115: No), the processing returns to step S111. On the other hand, if it is determined that the examination is completed (step S115: Yes), the processing ends.

It is noted that step S113 may be executed prior to step S112, and step S113 may be executed simultaneously with step S112.

As described above, in the first example, the doctor can switch the display of the polyp detection result according to the state of the patient's large intestine. Thus, it is possible to increase the accuracy of the polyp detection.

Second Example (Functional Configuration)

Figure 7:
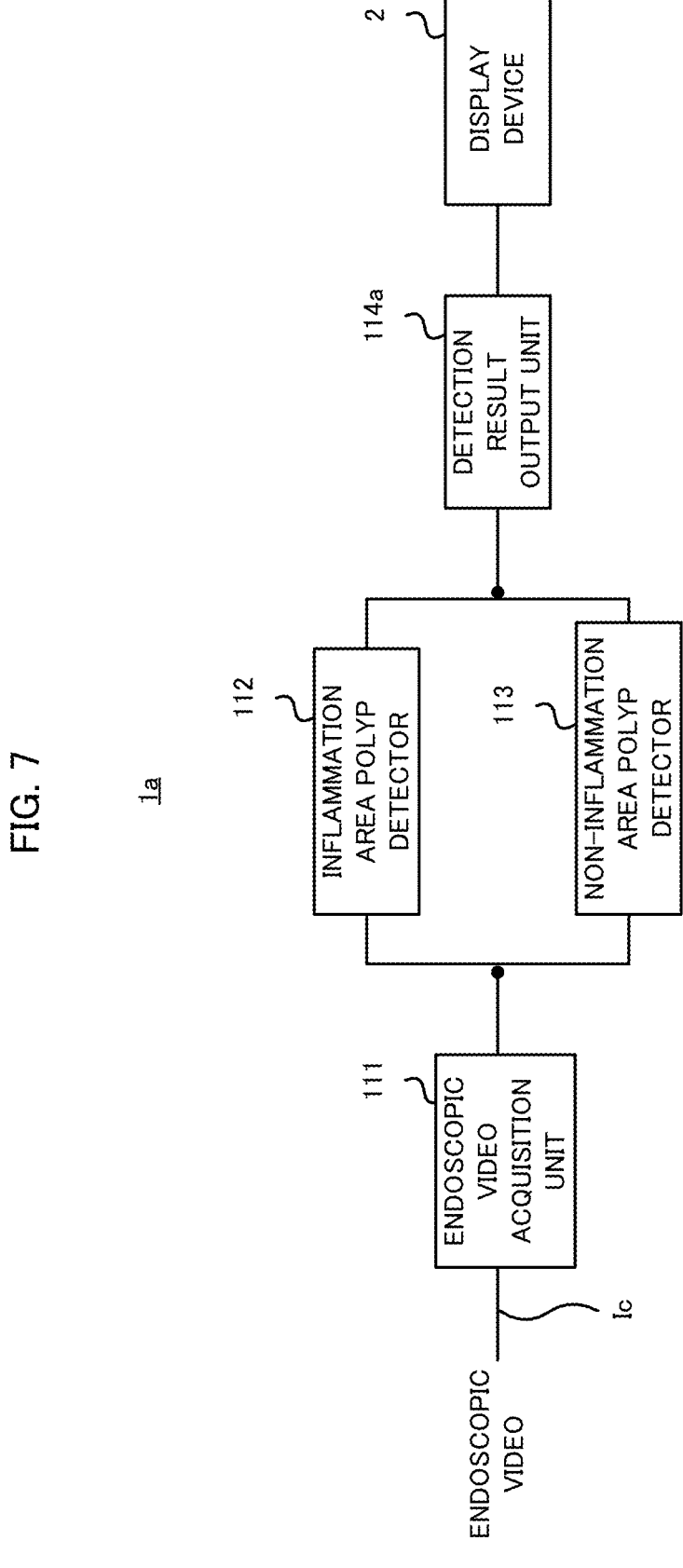
FIG. 7 is a block diagram showing a functional configuration of an endoscopic examination support apparatus according to a second example of the first example embodiment.

Next, a second example will be described. FIG. 7 is a block diagram illustrating a functional configuration of an endoscopic examination support apparatus 1a according to a second example. In the second example, although the configuration of the endoscopic examination support apparatus is the same as that of the first example, the processing content of the detection result output unit is different. Since the endoscopic video acquisition unit 111, the inflammation area polyp detector 112, and the non-inflammation area polyp detector 113 have the same configuration as the endoscopic examination support apparatus 1 of the first example and operate in the same manner, the description thereof will be omitted.

To the detection result output unit 114a, the inflammation area polyp detection result is inputted from the inflammation area polyp detector 112, and the non-inflammation area polyp detection result is inputted from the non-inflammation area polyp detector 113. The detection result output unit 114a compares the confidence score of the polyp included in the inflammation area polyp detection result with the confidence score of the polyp included in the non-inflammation area polyp detection result. Then, the detection result output unit 114a generates the display data using the polyp detection result of the higher confidence score, and outputs the display data to the display device 2.

(Image Display Processing)

Figure 8:
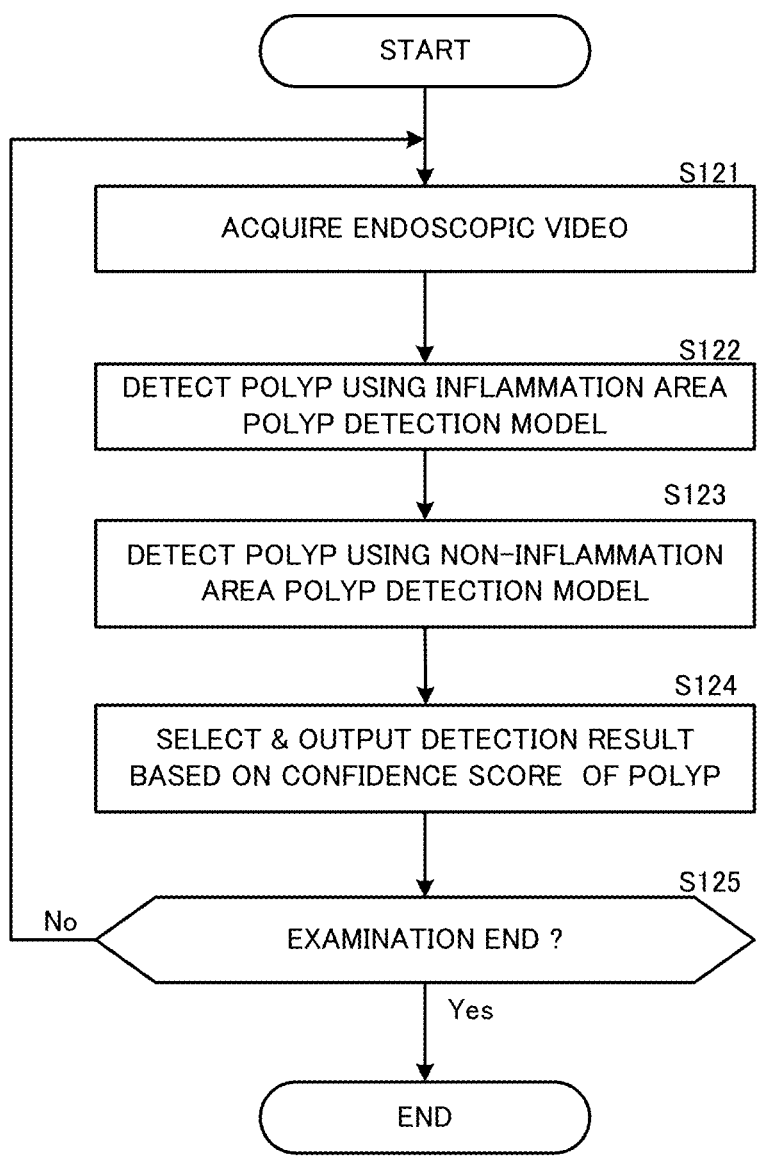
FIG. 8 is a flowchart of image display processing by the endoscopic examination support apparatus according to the second example of the first example embodiment.

FIG. 8 is a flowchart of the image display processing performed by the endoscopic examination support apparatus 1a. This processing is realized by the processor 11 shown in FIG. 2, which executes a pre-prepared program and operates as each element shown in FIG. 7. Since the processing of steps S121 to S123 and S125 is the same as the processing of steps S111 to S113 and S115 of the first example shown in FIG. 6, the description thereof will not be repeated.

The inflammation area polyp detection result obtained in step S122 and the non-inflammation area polyp detection result obtained in step S123 are outputted to the detection result output unit 114a. The detection result output unit 114a compares the confidence score of the polyp included in the inflammation area polyp detection result with the confidence score of the polyp included in the non-inflammation area polyp detection result. Then, the detection result output unit 114a generates the display data using the polyp detection result of the higher confidence score, and outputs the display data to the display device 2 (step S124).

As described above, in the second example, since the display of the polyp detection result can be switched based on the confidence score of the polyp, the operation of the doctor is not required, and the endoscopic examination can be efficiently performed.

Third Example (Functional Configuration)

Figure 9:
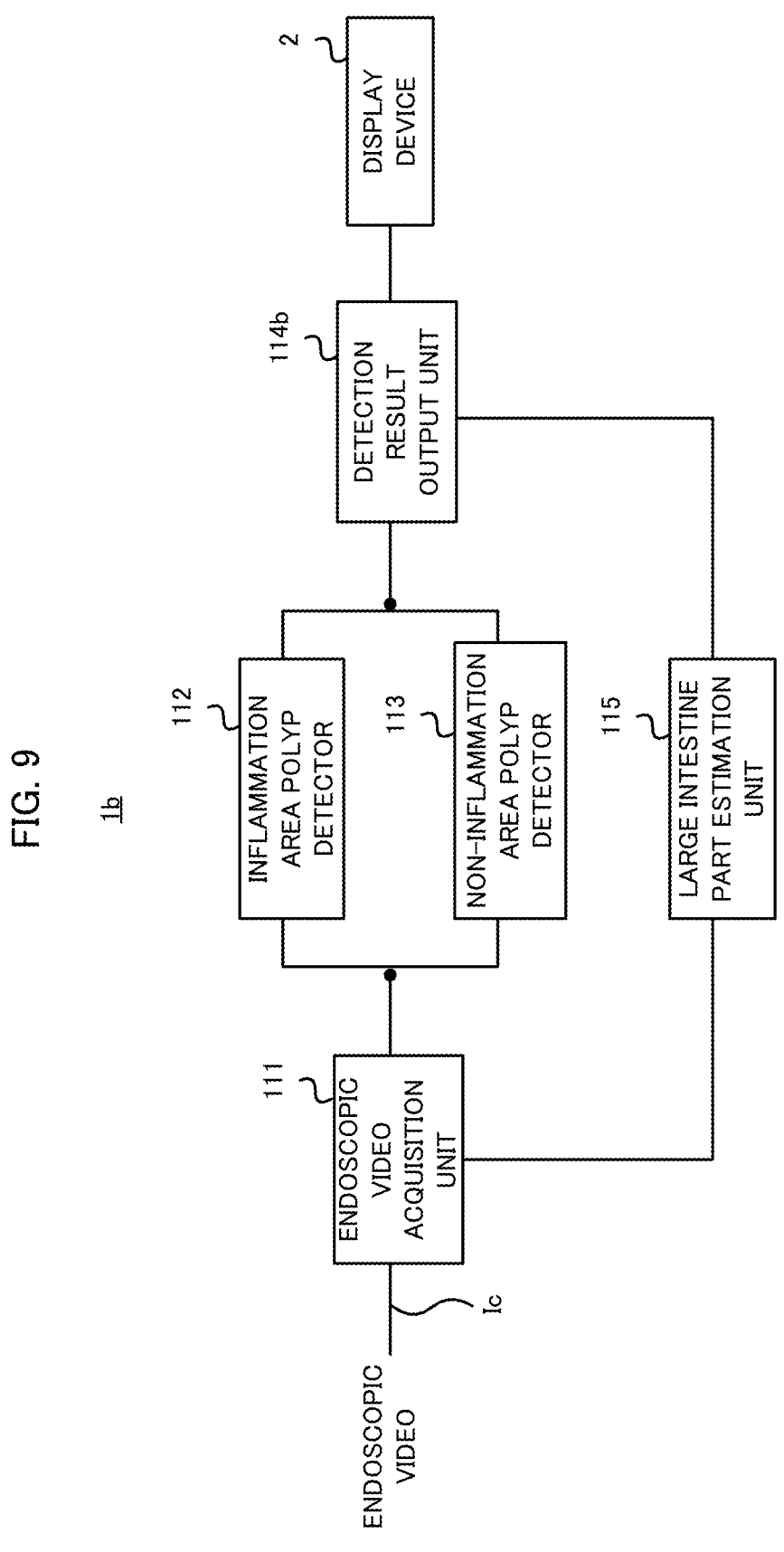
FIG. 9 is a block diagram showing a functional configuration of an endoscopic examination support apparatus according to a third example of the first example embodiment.

Next, a third example will be described. FIG. 9 is a block diagram illustrating a functional configuration of an endoscopic examination support apparatus 1b according to a third example. The third example is based on the endoscopic examination support apparatus 1 according to the first example, and further includes a large intestine part estimation unit 115. Since the inflammation area polyp detector 112 and the non-inflammation area polyp detector 113 have the same configuration as the endoscopic examination support apparatus 1 of the first example and operate in the same manner, the description thereof will be omitted.

The endoscopic examination support apparatus 1b receives an endoscopic video Ic from the endoscope 3. The endoscopic video Ic is inputted to the endoscopic video acquisition unit 111. The endoscopic video acquisition unit 111 outputs the inputted endoscopic video Ic to the inflammation area polyp detector 112, the non-inflammation area polyp detector 113, and the large intestine part estimation unit 115.

Figure 10:
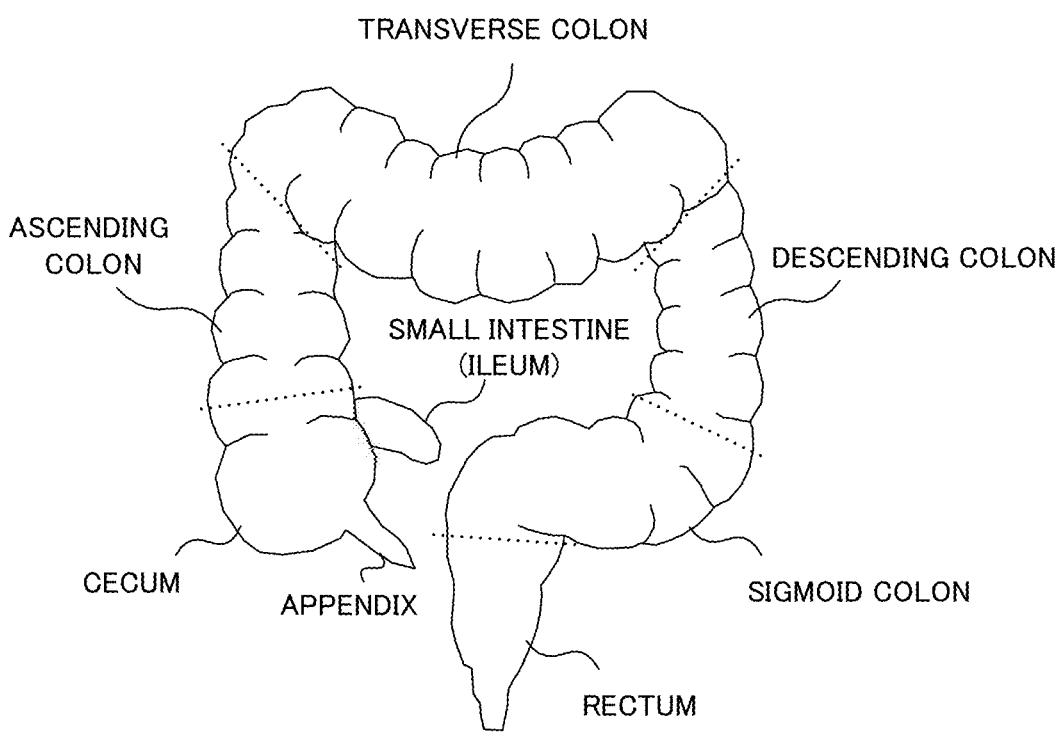
FIG. 10 schematically shows structure of a large intestine.

The endoscopic video Ic is inputted from the endoscopic video acquisition unit 111 to the large intestine part estimation unit 115. The large intestine part estimation unit 115 detects the position of the endoscope 3, i.e., the shooting position of the endoscopic video, based on the endoscopic video Ic. For example, the large intestine part estimation unit 115 may estimate the shooting position by image analysis of the inputted endoscopic video Ic, or may estimate the shooting position by reproducing the insertion shape of the endoscope 3 with a three-dimensional image. Here, the shooting position may be information indicating one of a plurality of areas in the organ to be examined. For example, as illustrated in FIG. 10, the large intestine includes multiple areas (parts) such as the cecum, the ascending colon, the transverse colon, the descending colon, the sigmoid colon, and the rectum. Therefore, when the examination target is the large intestine, it is sufficient that the large intestine part estimation unit 115 can detect which one of the above-described parts the shooting position belongs to. The large intestine part estimation unit 115 outputs the detected shooting position to the detection result output unit 114b.

To the detection result output unit 114b, the inflammation area polyp detection result is inputted from the inflammation area polyp detector 112, the non-inflammation area polyp detection result is inputted from the non-inflammation area polyp detector 113, and the shooting position is inputted from the large intestine part estimation unit 115.

The detection result output unit 114b selects at least one of the inflammation area polyp detection result and the non-inflammation area polyp detection result based on the shooting position. The correspondence between the shooting position and the polyp detection result to be selected is defined in advance. For example, the doctor can define in advance that the inflammation area polyp detection result is selected for the ascending colon, the sigmoid colon, and the rectum, and the non-inflammation area polyp detection result is selected for other parts. The above correspondence may be determined based on the likelihood of general inflammation for each large intestine part, or may be determined based on the condition of the patient. The detection result output unit 114b generates display data using the selected polyp detection result and outputs the display data to the display device 2.

(Image Display Processing)

Figure 11:
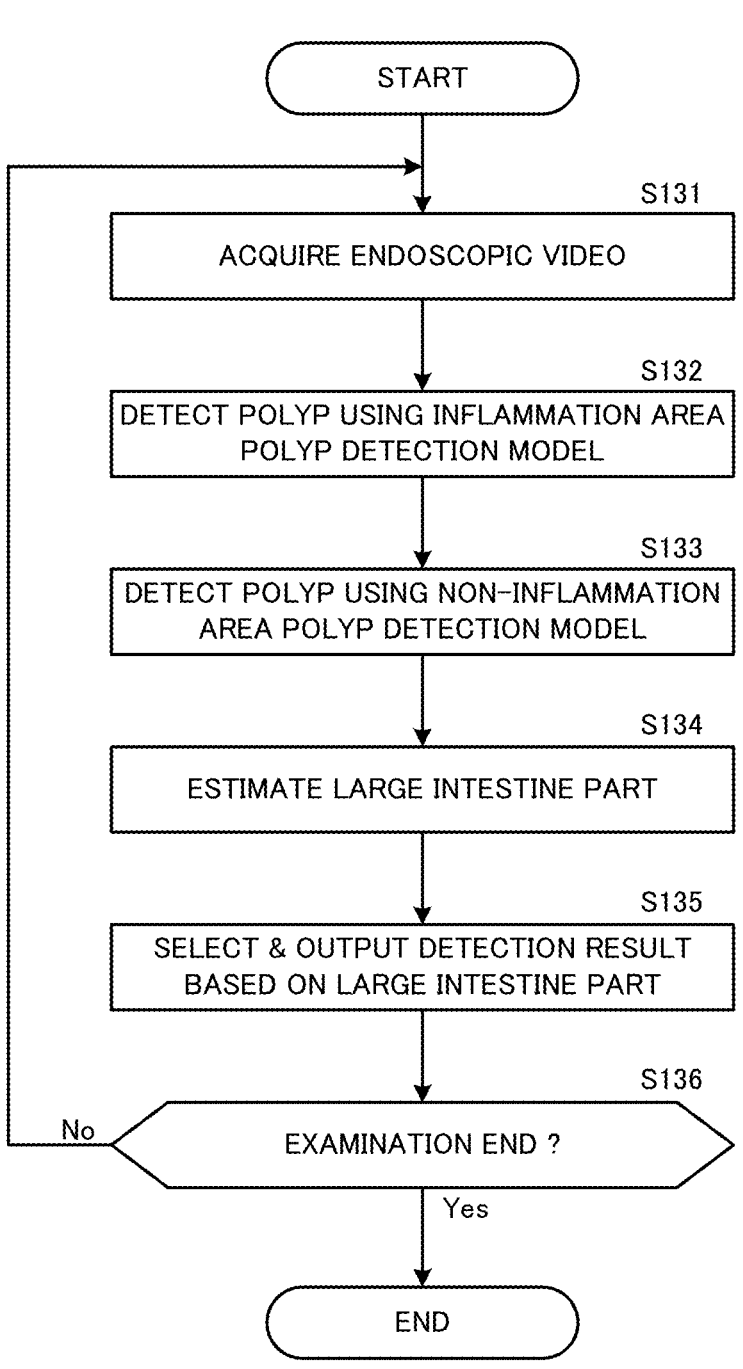
FIG. 11 is a flowchart of image display processing by the endoscopic examination support apparatus according to the third example of the first example embodiment.

FIG. 11 is a flowchart of the image display processing performed by the endoscopic examination support apparatus 1b. This processing is realized by the processor 11 shown in FIG. 2, which executes a pre-prepared program and operates as each element shown in FIG. 9. Since the processing of steps S131 to S133 and S136 is the same as the processing of steps S111 to S113 and S115 of the first example shown in FIG. 6, the description thereof will not be repeated.

The endoscopic video Ic obtained in step S131 is outputted to the large intestine part estimation unit 115. In addition, the inflammation area polyp detection result obtained in step S132 and the non-inflammation area polyp detection result obtained in step S133 are outputted to the detection result output unit 114*b*.

The large intestine part estimation unit 115 detects the shooting position of the endoscopic video based on the endoscopic video Ic. The large intestine part estimation unit 115 outputs the shooting position to the detection result output unit 114*b* (step S134).

The detection result output unit 114*b* selects at least one of the inflammation area polyp detection result and the non-inflammation area polyp detection result on the basis of the shooting position acquired from the large intestine part estimation unit 115. Then, the detection result output unit 114*b* generates display data using the selected polyp detection result, and outputs the display data to the display device 2 (step S135).

It is noted that step S134 may be executed before step S132 and S133, and step S134 may be executed simultaneously with step S132 or S133.

As described above, in the third example, since the display of the polyp detection result can be switched according to the shooting position of the large intestine, the operation of the doctor is not required, and the endoscopic examination can be efficiently performed.

Fourth Example (Functional Configuration)

Next, a fourth example will be described. FIG. 12 is a block diagram illustrating a functional configuration of an endoscopic examination support apparatus 1*c* according to a fourth example. The fourth example is based on the endoscopic examination support apparatus 1*b* according to the third example, and further includes a previous examination result acquisition unit 116. Incidentally, since the endoscopic video acquisition unit 111, the inflammation area polyp detector 112, the non-inflammation area polyp detector 113, and the large intestine part estimation unit 115 have the same configuration as the endoscopic examination support apparatus 1*b* of the third example and operate in the same manner, the explanation thereof will be omitted.

The previous examination result acquisition unit 116 acquires the previous endoscopic examination result of the subject from the DB 17. Specifically, the patient ID of the patient who is the subject is inputted to the endoscopic examination support apparatus 1*c* through the input unit 14. The patient ID is information that uniquely identify the patient, such as an ID uniquely given to each patient. The previous examination result acquisition unit 116 acquires the patient ID inputted through the input unit 14. Then, the previous examination result acquisition unit 116 acquires the previous endoscopic examination result corresponding to the patient ID from the DB 17.

In addition, the previous examination result acquisition unit 116 extracts the lesion information from the previous endoscopic examination results. The lesion information includes information on the shooting position where the polyp was detected and the state of the large intestine at that shooting position. The previous examination result acquisition unit 116 outputs the lesion information to the detection result output unit 114*c*.

To the detection result output unit 114*c*, the inflammation area polyp detection result is inputted from the inflammation area polyp detector 112, the non-inflammation area polyp detection result is inputted from the non-inflammation area polyp detector 113, the shooting position is inputted from the large intestine part estimation unit 115, and the lesion information is inputted from the previous examination result acquisition unit 116.

The detection result output unit 114*c* selects at least one of the inflammation area polyp detection result and the non-inflammation area polyp detection result based on the shooting position and the past lesion information. For example, when the polyp was detected in the inflammation area in the past examination, the detection result output unit 114*c* selects the inflammation area polyp detection result in the large intestine part in which the polyp was detected. Then, the detection result output unit 114*c* generates display data using the selected polyp detection result and outputs the display data to the display device 2.

(Image Display Processing)

Figure 13:
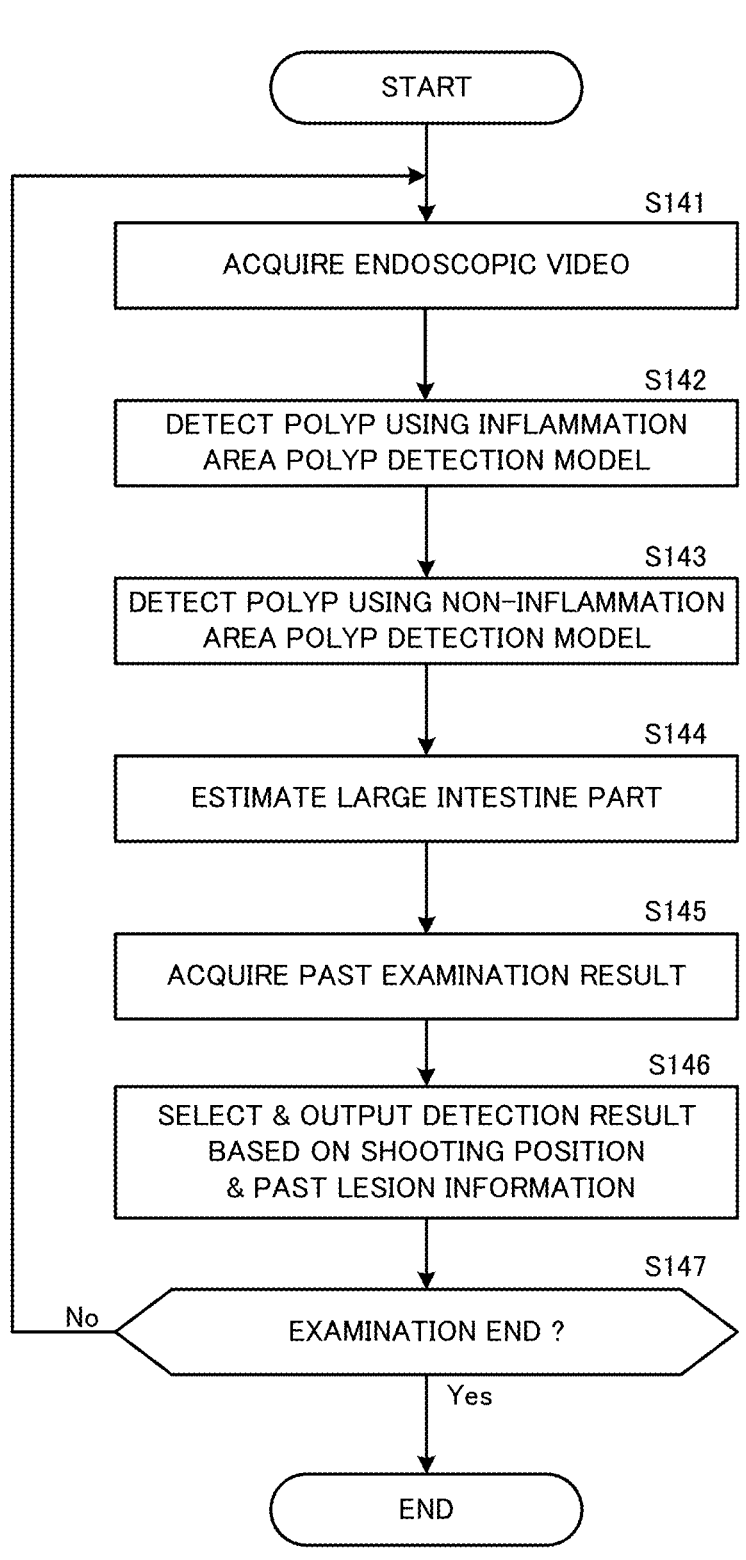
FIG. 13 is a flowchart of image display processing by the endoscopic examination support apparatus according to the fourth example of the first example embodiment.

FIG. 13 is a flowchart of the image display processing performed by the endoscopic examination support apparatus 1*c*. This processing is realized by the processor 11 shown in FIG. 2, which executes a pre-prepared program and operates as each element shown in FIG. 12. Since the processing of steps S141 to S144 and S147 is the same as the processing of the steps S131 to S134 and S136 of the third example shown in FIG. 11, the description thereof will not be repeated.

The inflammation area polyp detection result obtained in step S142, the non-inflammation area polyp detection result obtained in step S143, and the shooting position obtained in step S144 are outputted to the detection result output unit 114*c*.

The previous examination result acquisition unit 116 acquires the past endoscopic examination result of the subject from the DB 17. Then, the previous examination result acquisition unit 116 extracts the lesion information from the past endoscopic examination result, and outputs it to the detection result output unit 114*c* (step S145).

The detection result output unit 114*c* selects at least one of the inflammation area polyp detection result and the non-inflammation area polyp detection result based on shooting position and the past lesion information. Then, the detection result output unit 114*c* generates display data using the selected polyp detection result, and outputs it to the display device 2 (step S146).

It is noted that step S145 may be executed before step S142, S143 and S144, and step S145 may be executed simultaneously with step S142, S143 or S144.

As described above, in the fourth example, since the display of the polyp detection result can be switched in consideration of the previous examination result of the subject, it is possible to perform the examination efficiently.

MODIFICATIONS

Next, modifications of the first example embodiment will be described. The following modifications can be applied to the first example embodiment in appropriate combination.

Modification 1

In the first example embodiment, the endoscopic support apparatus switches the display of the polyp detection result based on whether or not inflammation has occurred in the large intestine. However, the application of the present disclosure is not limited this. For example, the endoscopic examination support apparatus may switch the display of the polyp detection result based on whether or not there is a diverticulum in the large intestine, or may switch the display of the polyp detection result based on whether or not there is a residue in the large intestine.

Modification 2

In the first example of the first example embodiment, the endoscopic examination support apparatus 1 switches the display of the polyp detection result based on the input information of the doctor. At this time, the endoscopic examination support apparatus 1 may associate the endoscopic video with the input information of the doctor and record them in the DB 17 or the like. By using the recorded contents as learning data, it is possible to generate a machine learning model which learned the relationship between the endoscopic image and the input information of the doctor. By switching the display of the polyp detection result based on the result estimated by this machine learning model, the operation of the doctor becomes unnecessary, and the endoscopic examination can be efficiently carried out.

Modification 3

In the third example of the first example embodiment, the detection result output unit 114b selects at least one of the inflammation area polyp detection result and the non-inflammation area polyp detection result based on the shooting position detected by the large intestine part estimation unit 115. Instead, the detection result output unit 114b may select the polyp detection result based on the inflammation degree of the large intestine. The inflammation degree of the large intestine is the value that indicates the level of inflammation in the large intestine.

Specifically, the endoscopic examination support apparatus 1b is provided with the inflammation degree estimation unit in place of the large intestine part estimation unit 115 in FIG. 9. The inflammation degree estimation unit estimates the inflammation degree from the endoscopic video Ic using the "inflammation degree estimation model" prepared in advance. Then, the inflammation degree estimation unit outputs the estimated inflammation degree to the detection result output unit 114b. Incidentally, the inflammation degree estimation model is a model that is learned using the training data in which the inflammation degree is given to the endoscopic image of the inflamed large intestine as a correct answer.

When the inflammation degree inputted from the inflammation degree estimation unit is equal to or larger than a predetermined threshold value, the detection result output unit 114b generates display data using the inflammation area polyp detection result and outputs it to the display device 2. On the other hand, when the inflammation degree inputted from the inflammation degree estimation unit is smaller than the predetermined threshold value, the detection result output unit 114b generates display data using the non-inflammation area polyp detection result and outputs it to the display device 2.

In the modification 3, since the display of the polyp detection result can be switched based on the inflammation degree of the large intestine, the operation of the doctor is not required, and the endoscopic examination can be efficiently performed.

Second Example Embodiment

Next, a description will be given of a second example embodiment. The endoscopic examination system 100 of the second example embodiment includes different lesion detectors, and can use the lesion detectors switched depending on the state of the large intestine. In the second example embodiment, since one of the lesion detectors is used, it is possible to reduce the processing load of the endoscopic examination support apparatus as compared with the first example embodiment. Note that the system configuration and the hardware configuration is the same as that of the first example embodiment, and the description thereof will be omitted.

First Example (Functional Configuration)

FIG. 14 is a block diagram illustrating a functional configuration of an endoscope examination support apparatus 20 according to a first example of the second example embodiment. The endoscopic examination support apparatus 20 functionally includes an endoscopic video acquisition unit 211, a detector selection unit 212, an inflammation area polyp detector 213, a non-inflammation area polyp detector 214, and a detection result output unit 215, in addition to the display device 2. Since the inflammation area polyp detector 213 and the non-inflammation area polyp detector 214 have the same configuration as the inflammation area polyp detector 112 and the non-inflammation area polyp detector 113 of the endoscopic examination support apparatus 1 according to the first example embodiment and operate in the same manner, the description thereof will be omitted.

The endoscopic video Ic is inputted from the endoscope 3 to the endoscopic examination support apparatus 20. The endoscopic video Ic is inputted to the endoscopic video acquisition unit 211. The endoscopic video acquisition unit 211 outputs the inputted endoscopic video Ic to the inflammation area polyp detector 213 or the non-inflammation area polyp detector 214 according to the selection by the detector selection unit 212, which will be described below.

The detector selection unit 212 acquires the input information of the doctor. Here, the input information of the doctor includes instruction information for switching of the polyp detectors. Specifically, the doctor operates the touch panel of the endoscopic examination support apparatus 20 or the operation unit 36 of the endoscope 3 to input the instruction information indicating one of the inflammation area polyp detector 213 and the non-inflammation area polyp detector 214 to be used. Incidentally, the input of instruction information by the doctor is performed at any timing during the endoscopic examination.

The detector selection unit 212 selects the polyp detector based on the input information of the doctor. Specifically, the detector selection unit 212 switches between the inflammation area polyp detector 213 and the non-inflammation area polyp detector 214 based on the input information of the doctor. For example, if the doctor instructs the use of the inflammation area polyp detector 213, the detector selection unit 212 performs the switching so that the endoscopic video acquisition unit 211 and the detection result output unit 215 are connected to the inflammation area polyp detector 213.

The polyp detector selected by the detector selection unit 212 (hereinafter, also referred to as "selected polyp detector") detects the polyp from the endoscopic video Ic and outputs the detection result to the detection result output unit 215.

The detection result output unit 215 acquires the polyp detection result from the selected polyp detector. Then, the detection result output unit 215 generates display data using the polyp detection result and outputs it to the display device 2.

(Image Display Processing)

Figure 15:
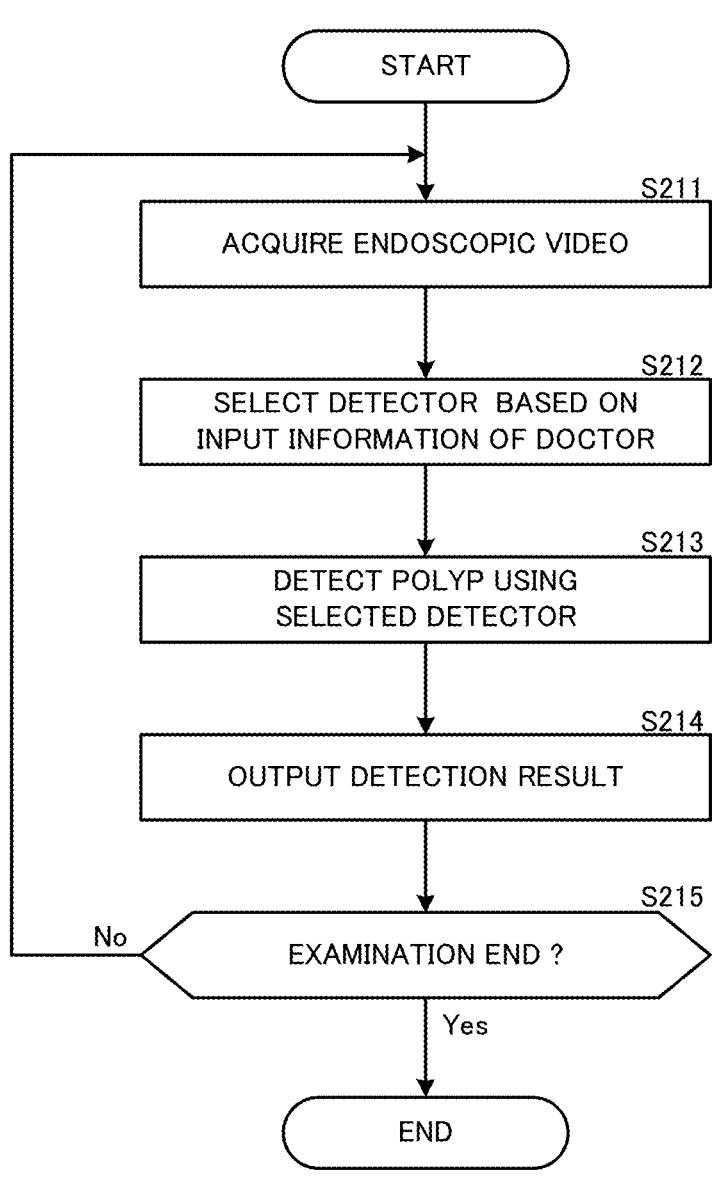
FIG. 15 is a flowchart of image display processing by the endoscopic examination support apparatus according to the first example of the second example embodiment.

FIG. 15 is a flowchart of the image display processing performed by the endoscopic examination support apparatus 20. This processing is realized by the processor 11 shown in FIG. 2, which executes a pre-prepared program and operates as each element shown in FIG. 14.

First, the endoscopic video Ic is inputted from the endoscope 3 to the endoscopic examination support apparatus 20. The endoscopic video acquisition unit 211 acquires the endoscopic video Ic. The endoscopic video acquisition unit 211 outputs the inputted endoscopic video Ic to one of the inflammation area polyp detector 213 and the non-inflammation area polyp detector 214 according to the selection by the detector selection unit 212 (step S211).

The detector selection unit 212 acquires input information of the doctor. The detector selection unit 212 selects the polyp detector based on the input from the doctor (step S212). When the selected polyp detector detects the polyp from the endoscopic video Ic, it outputs the detection result to the detection result output unit 215 (step S213). Next, the detection result output unit 215 generates the display data using the polyp detection result and outputs the display data to the display device 2 (step S214). Next, the endoscopic examination support apparatus 20 determines whether the examination is completed or not. If it is determined that the examination is not completed (step S215: No), the processing returns to step S211. On the other hand, if it is determined that the examination is completed (step S215: Yes), the processing ends.

As described above, in the first example, the doctor can switch the polyp detector according to the state of the patient's large intestine. Thus, it is possible to increase the accuracy of the polyp detection.

Second Example (Functional Configuration)

Next, a second example will be described. FIG. 16 is a block diagram illustrating a functional configuration of an endoscopic examination support apparatus 20b according to a second example. The second example is based on the first example of the endoscopic examination support apparatus 20, and further includes a large intestine part estimation unit 216. The large intestine part estimation unit 216 operates in the same manner as the large intestine part estimation unit 115 of the first example embodiment.

Since the inflammation area polyp detector 213, the non-inflammation area polyp detector 214, and the detection result output unit 215 have the same configuration as the endoscopic examination support apparatus 20 of the first example and operate in the same manner, the description thereof will be omitted.

To the endoscopic examination support apparatus 20b, an endoscopic video Ic is inputted from the endoscope 3. The endoscopic video Ic is inputted to the endoscopic video acquisition unit 211. The endoscopic video acquisition unit 211 outputs the inputted endoscopic video Ic to the large intestine part estimation unit 216. Also, the endoscopic video acquisition unit 211 outputs the inputted endoscopic video Ic to one of the inflammation area polyp detector 213 and the non-inflammation area polyp detector 214 according to the selection by the detector selection unit 212b, which will be described later.

The endoscopic video Ic is inputted from the endoscopic video acquisition unit 211 to the large intestine part estimation unit 216. Based on the endoscopic video Ic, the large intestine part estimation unit 216 detects the position of the endoscope 3, i.e., the shooting position of the endoscopic video. The large intestine part estimation unit 216 outputs the estimated shooting position to the detector selection unit 212b.

The detector selection unit 212b selects the polyp detector on the basis of the shooting position acquired from the large intestine part estimation unit 216. The correspondence between the shooting position and the polyp detector to be selected is defined in advance. For example, the doctor can define in advance to select the inflammation area polyp detector 213 for the ascending colon, the sigmoid colon and the rectum, and selects the non-inflammation area polyp detector 214 for other parts. The selected polyp detector detects the polyp from the endoscopic video Ic and outputs the detection result to the detection result output unit 215.

(Image Display Processing)

Figure 17:
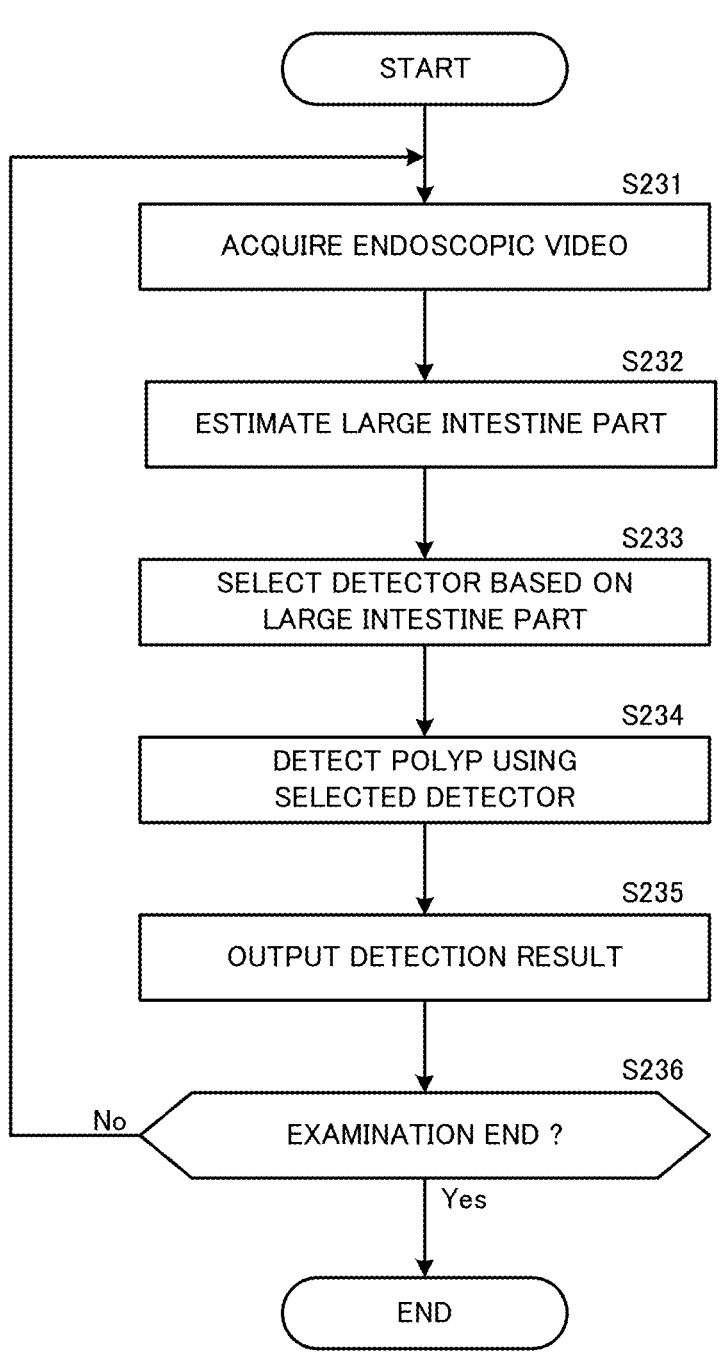
FIG. 17 is a flowchart of image display processing by the endoscopic examination support apparatus according to the second example of the second example embodiment.

FIG. 17 is a flowchart of the image display processing performed by the endoscopic examination support apparatus 20b. This processing is realized by the processor 11 shown in FIG. 2, which executes a pre-prepared program and operates as each element shown in FIG. 16.

First, the endoscopic video Ic is inputted from the endoscope 3 to the endoscopic examination support apparatus 20b. The endoscopic video acquisition unit 211 acquires the endoscopic video Ic. The endoscopic video acquisition unit 211 outputs the inputted endoscopic video Ic to the large intestine part estimation unit 216 (step S231).

Next, the large intestine part estimation unit 216 detects the shooting position of the endoscopic image based on the endoscopic video Ic. The large intestine part estimation unit 216 outputs the shooting position to the detector selection unit 212b (step S232).

Next, the detector selection unit 212b selects the polyp detector on the basis of the shooting position acquired from the large intestine part area estimation unit 216 (step S233). According to the selection by the detector selection unit 212b, the endoscopic video acquisition unit 211 outputs the inputted endoscopic video Ic to the inflammation area polyp detector 213 or the non-inflammation area polyp detector 214. The polyp detector selected by the detector selection unit 212b detects the polyp from the endoscopic video Ic and outputs the detection result to the detection result output unit 215 (step S234). Next, the detection result output unit 215 generates the display data using the polyp detection result and outputs the display data to the display device 2 (step S235).

Next, the endoscopic examination support apparatus 20b determines whether or not the examination is completed. If it is determined that the examination is not completed (step S236: No), the processing returns to step S231. On the other hand, if it is determined that the examination is completed (step S236: Yes), the processing ends.

As described above, in the second example, since the polyp detector can be switched according to the shooting position of the large intestine, the operation of the doctor is not required, and it is possible to perform the endoscopic examination efficiently.

Third Example (Functional Configuration)

Figure 18:
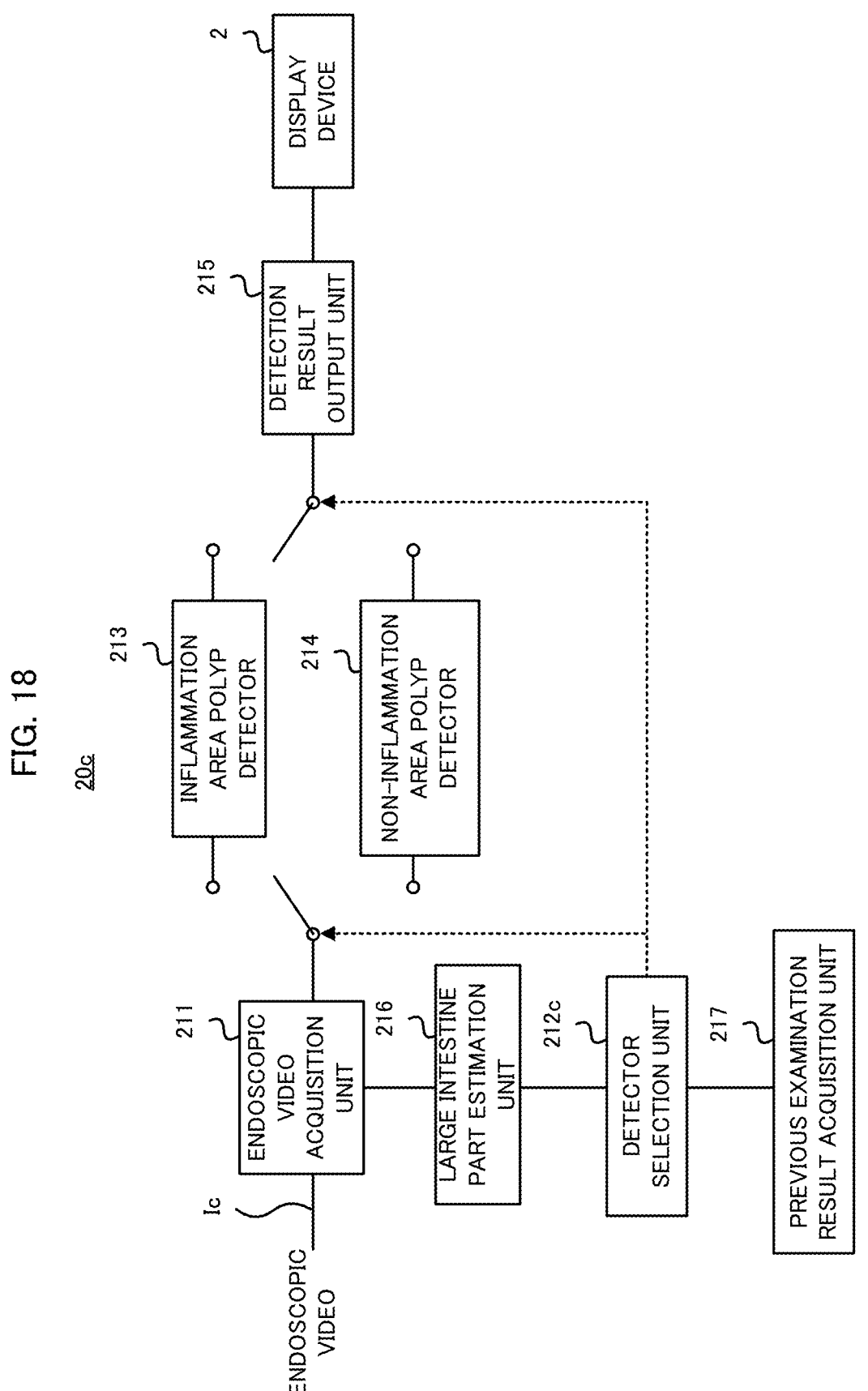
FIG. 18 is a block diagram showing a functional configuration of an endoscopic examination support apparatus according to a third example of the second example embodiment.

Next, a third example will be described. FIG. 18 is a block diagram illustrating a functional configuration of an endoscopic examination support apparatus 20c according to a third example. The third example embodiment is based on the endoscopic examination support apparatus 20b according to the second example, and further includes a previous examination result acquisition unit 217. The previous examination result acquisition unit 217 operates similarly to the previous examination result acquisition unit 116 of the first example embodiment.

Incidentally, the endoscopic video acquisition unit 211, the inflammation area polyp detector 213, the non-inflammation area polyp detector 214, the detection result output unit 215, and the large intestine part estimation unit 216 have the same configuration as the endoscopic examination support apparatus 20*b* of the second example and operate in the same manner. Therefore, the explanation thereof will be omitted.

The previous examination result acquisition unit 217 acquires the past endoscopic examination result of the subject from the DB 17. Then, the previous examination result acquisition unit 217 extracts the lesion information from the past endoscopic examination result. The lesion information includes information on the shooting position where the polyp was detected and the state of the large intestine at that shooting position. The previous examination result acquisition unit 217 outputs the lesion information to the detector selection unit 212*c*.

To the detector selection unit 212*c*, the shooting position is inputted from the large intestine part estimation unit 216 and and the past lesion information is inputted from the previous examination result acquisition unit 217. The detector selection unit 212*c* selects the polyp detector based on the shooting position and the past lesion information. For example, when a polyp was detected in the inflammation area in the past examination, the detector selection unit 212*c* selects the inflammation area polyp detector 213 in the area of the large intestine in which the polyp was detected. The selected polyp detector detects the polyp from the endoscopic video Ic and outputs the detection result to the detection result output unit 215.

(Image Display Processing)

FIG. 19 is a flowchart of the image display processing performed by the endoscopic examination support apparatus 20*c*. This processing is realized by the processor 11 shown in FIG. 2, which executes a pre-prepared program and operates as each element shown in FIG. 18. Since the processing of steps S241 to S242 and S245 to S247 is the same as the processing of steps S231 to S232 and S234 to S236 of the second example shown in FIG. 17, the description thereof will not be repeated.

The shooting position obtained in step S242 is outputted to the detector selection unit 212*c*. In addition, the previous examination result acquisition unit 217 acquires the past endoscopic examination result of the subject from the DB 17. Then, the previous examination result acquisition unit 217 extracts the lesion information from the past endoscopic examination result, and outputs it to the detector selection unit 212*c* (step S243). Next, the detector selection 212*c* selects the polyp detector based on the shooting position and the past lesion information (step S244).

As described above, in the third example, since the polyp detector can be switched in consideration of the previous examination result of the subject, it is possible to perform the examination efficiently.

MODIFICATIONS

Next, modifications of the second example embodiment will be described. The following modifications can be applied to the second example embodiment in appropriate combination.

Modification 1

In the second example embodiment, the endoscopic support apparatus switches the polyp detectors based on whether or not inflammation has occurred in the large intestine. However, the application of the present disclosure is not limited this. For example, the endoscopic examination support apparatus may switch the polyp detectors based on whether or not there is a diverticulum in the large intestine, or may switch the polyp detectors based on whether or not there is a residue in the large intestine.

Modification 2

In the first example of the second example embodiment, the endoscopic examination support apparatus 1 switches the polyp detectors based on the input information from a doctor. At this time, the endoscopic examination support apparatus 1 may associate the endoscopic video with the input information of the doctor and record them in the DB 17 or the like. By using the recorded contents as learning data, it is possible to generate a machine learning model which learned the relationship between the endoscopic video and the input information of the doctor. By switching the polyp detector on the basis of the estimation result of this machine learning model, the operation of the doctor becomes unnecessary, and it becomes possible to carry out the endoscopic examination efficiently.

Modification 3

In the second example of the second example embodiment, the detector selection unit 212*b* selects the polyp detector based on the shooting position detected by the large intestine part estimation unit 216. Instead, the detector selection unit 212*b* may select the polyp detector based on the inflammation degree of the large intestine.

Specifically, the endoscopic examination support apparatus 20*b* is provided with an inflammation degree estimation unit in place of the large intestine part estimation unit 216 of FIG. 16. The inflammation degree estimation unit estimates the inflammation degree from the endoscopic video Ic using the "inflammation degree estimation model" prepared in advance. Then, the inflammation degree estimation unit outputs the estimated inflammation degree to the detector selection unit 212*b*. When the inflammation degree inputted from the inflammation degree estimation unit is equal to or larger than a predetermined threshold, the detector selection unit 212*b* selects the inflammation area polyp detector 213. On the other hand, when the inflammation degree inputted from the inflammation degree estimation unit is smaller than the predetermined threshold, the detector selection unit 212*b* selects the non-inflammation area polyp detector 214.

In the modification 3, since the polyp detector can be switched based on the inflammation degree of the large intestine, the operation of the doctor is not required, and the endoscopic examination can be efficiently performed.

Third Example Embodiment

Figure 20:
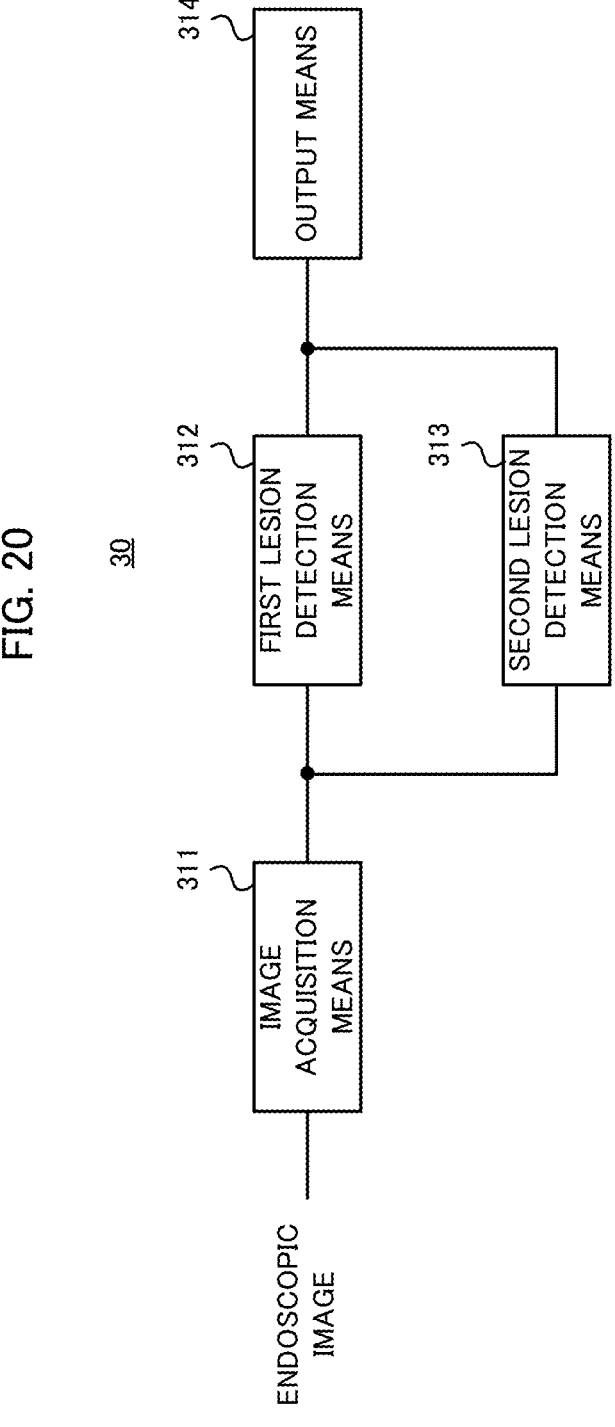
FIG. 20 is a block diagram showing a functional configuration of an endoscopic examination support apparatus according to a third example embodiment.

FIG. 20 is a block diagram illustrating a functional configuration of an endoscopic examination support apparatus according to a third example embodiment. The endoscopic examination support apparatus 30 includes an image acquisition means 311, a first lesion detection means 312, a second lesion detection means 313, and an output means 314.

FIG. 21 is a flowchart illustrating processing performed by the endoscopic examination support apparatus 30 according to the third example embodiment. The image acquisition means 311 acquires an endoscopic image taken by an endoscope (step S311). The first lesion detection means 312 detects a lesion candidate from the endoscopic image, using a machine learning model that learned a relationship between the lesion candidate and a normal state of a large intestine (step S312). The second lesion detection means 313 detects a lesion candidate from the endoscopic image, using a machine learning model that learned a relationship between the lesion candidate and a predetermined state of the large intestine (step S313). The output means 314 outputs at least one of a detection result of the first lesion detection means and a detection result of the second lesion detection means (step S314).

According to the endoscopic examination support apparatus 30 of the third example embodiment, during the endoscopic examination, it is possible to advance the examination while switching the lesion detector in accordance with the state of the large intestine.

A part or all of the example embodiments described above may also be described as the following supplementary notes, but not limited thereto.

(Supplementary Note 1)

An endoscopic examination support apparatus comprising:

an image acquisition means configured to acquire an endoscopic image taken by an endoscope;

a first lesion detection means configured to detect a lesion candidate from the endoscopic image, using a machine learning model that learned a relationship between the lesion candidate and a normal state of a large intestine;

a second lesion detection means configured to detect a lesion candidate from the endoscopic image, using a machine learning model that learned a relationship between the lesion candidate and a predetermined state of the large intestine; and an output means configured to output at least one of a detection result of the first lesion detection means and a detection result of the second lesion detection means.

(Supplementary Note 2)

The endoscopic examination support apparatus according to Supplementary note 1, wherein the output means selects and outputs one of the detection result of the first lesion detection means and the detection result of the second lesion detection means having higher confidence.

(Supplementary Note 3)

The endoscope examination support apparatus according to Supplementary note 1, further comprising a large intestine part estimation means configured to estimate a part of the large intestine, wherein the output means selects one of the detection result of the first lesion detection means and the detection result of the second lesion detection means according to the estimated part of the large intestine.

(Supplementary Note 4)

The endoscope examination support apparatus according to Supplementary note 3, further comprising an examination result acquisition means configured to acquire a previous examination result, wherein the previous examination result includes information of the lesion candidate detected in an inflammation area, and wherein the output means selects and outputs one of the detection result of the first lesion detection means and the detection result of the second lesion detection means based on the estimated part of the large intestine and the previous examination result.

(Supplementary Note 5)

The endoscopic examination support apparatus according to Supplementary note 1, further comprising:

a selection means configured to select one of the first lesion detection means and the second lesion detection means to detect the lesion candidate; and a large intestine part estimation means configured to estimate a part of the large intestine, wherein the selection means selects one of the first lesion detection means and the second lesion detection means to detect the lesion candidate based on the estimated part of the large intestine.

(Supplementary Note 6)

The endoscopic examination support apparatus according to Supplementary note 5, further comprising an examination result acquisition means configured to acquire a previous examination result, wherein the previous examination result includes information of the lesion candidates detected in an inflammation area, and wherein the selection means causes one of the first lesion detection means and the second lesion detection means to perform detection based on the estimated part of the large intestine and the previous examination result.

(Supplementary Note 7)

The endoscopic examination support apparatus according to Supplementary note 1, wherein the predetermined state of the large intestine is an inflammation state, and wherein the second lesion detection means detects the lesion candidate using a machine learning model that learned a relationship between the lesion candidate and an inflammation state of the large intestine.

(Supplementary Note 8)

The endoscope examination support apparatus according to Supplementary note 7, further comprising an inflammation degree estimation means configured to estimate an inflammation degree of the large intestine based on the endoscopic image, wherein the output means selects and outputs one of the detection result of the first lesion detection means and the detection result of the second lesion detection means according to the estimated inflammation degree of the large intestine.

(Supplementary Note 9)

The endoscopic examination support apparatus according to Supplementary note 1, wherein the predetermined state of the large intestine is a state in which there is a residue in the large intestine, and wherein the second lesion detection means detects the lesion candidate using a machine learning model that learned a relationship between the lesion candidate and a state of the large intestine with a residue.

(Supplementary Note 10)

The endoscopic examination support apparatus according to Supplementary note 1, wherein the predetermined state of the large intestine is a state in which there is a diverticulum in the large intestine, and wherein the second lesion detection means detects the lesion candidate using a machine learning model that learned a relationship between the lesion candidate and a state of the large intestine with a diverticulum.

21

(Supplementary Note 11)

An endoscopic examination support method comprising:

acquiring an endoscopic image taken by an endoscope;

detecting a lesion candidate from the endoscopic image, using a machine learning model that learned a relation-ship between the lesion candidate and a normal state of a large intestine;

detecting a lesion candidate from the endoscopic image, using a machine learning model that learned a relation-ship between the lesion candidate and a predetermined state of the large intestine; and outputting at least one of two detection results of the lesion candidate.

(Supplementary Note 12)

A recording medium storing a program, the program causing a computer to perform processing of:

acquiring an endoscopic image taken by an endoscope;

detecting a lesion candidate from the endoscopic image, using a machine learning model that learned a relation-ship between the lesion candidate and a normal state of a large intestine;

detecting a lesion candidate from the endoscopic image, using a machine learning model that learned a relation-ship between the lesion candidate and a predetermined state of the large intestine; and outputting at least one of two detection results of the lesion candidate.

While the present disclosure has been described with reference to the example embodiments and examples, the present disclosure is not limited to the above example embodiments and examples. Various changes which can be understood by those skilled in the art within the scope of the present disclosure can be made in the configuration and details of the present disclosure.

DESCRIPTION OF SYMBOLS

1 Endoscopic examination support apparatus

2 Display device

3 Endoscope

11 Processor

12 Memory

17 Database (DB)

100 Endoscopic examination system

111 Endoscopic video acquisition unit

112 Inflammation area polyp detector

113 Non-inflammation area polyp detector

114 Detection result output unit

115 Large intestine part estimation unit

116 Previous examination result acquisition unit

What is claimed is:

1. An endoscopic examination support apparatus com-prising:

a memory configured to store instructions; and a processor configured to execute the instructions to:

acquire an endoscopic image taken by an endoscope;

detect a lesion candidate from the endoscopic image, using a first machine learning model that learned a relationship between the lesion candidate and a normal state of a large intestine;

detect a lesion candidate from the endoscopic image, using a second machine learning model that learned a relationship between the lesion candidate and a prede-termined state of the large intestine; and output at least one of a detection result obtained using the first machine learning model and a detection result obtained using the second machine learning model

22 wherein the predetermined state of the large intestine is an inflammation state, and wherein the processor detects the lesion candidate using the second machine learning model that learned a relationship between the lesion candidate and an inflammation state of the large intestine.

2. The endoscopic examination support apparatus accord-ing to claim 1, wherein the processor selects and outputs one of the detection result obtained using the first machine learning model and the detection result obtained using the second machine learning model having higher confidence.

3. The endoscope examination support apparatus accord-ing to claim 1, wherein the processor is further configured to execute the instructions to estimate a part of the large intestine, wherein the processor selects one of the detection result obtained using the first machine learning model and the detection result obtained using the second machine learning model according to the estimated part of the large intestine.

4. The endoscope examination support apparatus accord-ing to claim 3, wherein the processor is further configured to execute the instructions to acquire a previous examination result, wherein the previous examination result includes infor-mation of the lesion candidate detected in an inflam-mation area, and wherein the processor selects and outputs one of the detection result obtained using the first machine learn-ing model and the detection result obtained using the second machine learning model based on the estimated part of the large intestine and the previous examination result.

5. The endoscopic examination support apparatus accord-ing to claim 1, wherein the processor is further configured to execute the instructions to:

select one of the first machine learning model and the second machine learning model to detect the lesion candidate; and estimate a part of the large intestine, wherein the processor selects one of the first machine learning model and the second machine learning model to detect the lesion candidate based on the estimated part of the large intestine.

6. The endoscopic examination support apparatus accord-ing to claim 5, wherein the processor is further configured to execute the instructions to acquire a previous examination result, wherein the previous examination result includes infor-mation of the lesion candidates detected in an inflam-mation area, and wherein the processor causes one of the first machine learning model and the second machine learning model to perform detection based on the estimated part of the large intestine and the previous examination result.

7. The endoscope examination support apparatus accord-ing to claim 1, wherein the processor is further configured to execute the instructions to estimate an inflammation degree of the large intestine based on the endoscopic image, wherein the processor selects and outputs one of the detection result obtained using the first machine learn-ing model and the detection result obtained using the second machine learning model according to the esti-mated inflammation degree of the large intestine.

8. The endoscopic examination support apparatus according to claim 1, wherein the predetermined state of the large intestine is a state in which there is a residue in the large intestine, and wherein the processor detects the lesion candidate using the second machine learning model that learned a relationship between the lesion candidate and a state of the large intestine with a residue.

9. The endoscopic examination support apparatus according to claim 1, wherein the predetermined state of the large intestine is a state in which there is a diverticulum in the large intestine, and wherein the processor detects the lesion candidate using the second machine learning model that learned a relationship between the lesion candidate and a state of the large intestine with a diverticulum.

10. The endoscopic examination support apparatus according to claim 1, wherein the processor outputs the detection result as a guide to a position of the lesion candidate for supporting decision making of a doctor.

11. An endoscopic examination support method comprising:

acquiring an endoscopic image taken by an endoscope;

detecting a lesion candidate from the endoscopic image, using a first machine learning model that learned a relationship between the lesion candidate and a normal state of a large intestine;

detecting a lesion candidate from the endoscopic image, using a second machine learning model that learned a relationship between the lesion candidate and a predetermined state of the large intestine; and outputting at least one of a detection result obtained using the first machine learning model and a detection result obtained using the second machine learning model wherein the predetermined state of the large intestine is an inflammation state, and wherein the second machine learning model is a model that learned a relationship between the lesion candidate and an inflammation state of the large intestine.

12. A non-transitory computer-readable recording medium storing a program, the program causing a computer to perform processing of:

acquiring an endoscopic image taken by an endoscope;

detecting a lesion candidate from the endoscopic image, using a first machine learning model that learned a relationship between the lesion candidate and a normal state of a large intestine;

detecting a lesion candidate from the endoscopic image, using a second machine learning model that learned a relationship between the lesion candidate and a predetermined state of the large intestine; and outputting at least one of a detection result obtained using the first machine learning model and a detection result obtained using the second machine learning model wherein the predetermined state of the large intestine is an inflammation state, and wherein the second machine learning model is a model that learned a relationship between the lesion candidate and an inflammation state of the large intestine.

* * * * *